(12) United States Patent
Cha

(10) Patent No.: US 11,925,815 B2
(45) Date of Patent: Mar. 12, 2024

(54) LIGHT IRRADIATING TOOTHBRUSH HAVING MULTIPLE LIGHT SOURCES ARRANGED IN ALTERNATION

(71) Applicant: Hee Chan Cha, Seoul (KR)

(72) Inventor: Hee Chan Cha, Seoul (KR)

( * ) Notice: Subject to any disclaimer, the term of this patent is extended or adjusted under 35 U.S.C. 154(b) by 0 days.

(21) Appl. No.: 17/579,874

(22) Filed: Jan. 20, 2022

(65) Prior Publication Data

US 2022/0134130 A1 May 5, 2022

Related U.S. Application Data

(63) Continuation-in-part of application No. 16/400,883, filed on May 1, 2019, now Pat. No. 11,241,588, (Continued)

(30) Foreign Application Priority Data

Nov. 21, 2012 (KR) .......................... 10-2012-0132261

(51) Int. Cl.
*A61N 5/06* (2006.01)
*A46B 9/04* (2006.01)
(Continued)

(52) U.S. Cl.
CPC .............. *A61N 5/0624* (2013.01); *A46B 9/04* (2013.01); *A46B 9/06* (2013.01); *A46B 15/0036* (2013.01); *A46D 1/0207* (2013.01); *A61C 17/225* (2013.01); *A61H 13/00* (2013.01); *A61N 5/0603* (2013.01); *A46B 2200/1026* (2013.01); *A46B 2200/1066* (2013.01); *A61C 17/3481* (2013.01); *A61H 2201/0153* (2013.01); *A61H 2201/10* (2013.01); *A61H 2201/1207* (2013.01); *A61H 2201/1657* (2013.01);
(Continued)

(58) Field of Classification Search
CPC ...... A61N 5/0624; A61N 5/0603; A46B 9/04; A46B 9/06; A46B 15/0036; A46B 15/0002; A46B 5/0095; A61C 17/225; A61C 1/0046; A61C 17/3481; A61H 13/00; A46D 1/0207
USPC ......... 15/22.1, 105, 110, 167.1; 433/29, 216
See application file for complete search history.

(56) References Cited

U.S. PATENT DOCUMENTS 5,836,033 A * 11/1998 Berge ................... A46B 9/06
15/207.2
7,269,873 B2 9/2007 Brewer et al.
(Continued)

FOREIGN PATENT DOCUMENTS

EP 3373171 A1 * 9/2018 ........... A61B 5/0077

*Primary Examiner* — Katina N. Henson
(74) *Attorney, Agent, or Firm* — WHDA, LLP

(57) ABSTRACT

Provided is a light irradiated toothbrush, in which light sources, irradiating light having mutually different wavelengths, are arranged in alternation at the bottom of waveguide bristles so that light of different wavelengths give rise to constructive interference which strengthens the intensity of the irradiated light, and the height of the light sources are varied on the basis of the wavelength of the light irradiated therefrom so as to effectively transmit light of short wavelengths to the waveguide bristles, and light having mutually different wavelengths are transmitted by means of the waveguide bristles, thereby effectively transmitting the light to the mouth of a user.

16 Claims, 17 Drawing Sheets

Related U.S. Application Data which is a continuation of application No. 14/646,397, filed as application No. PCT/KR2013/005355 on Jun. 18, 2013, now abandoned.

(51) Int. Cl.
    *A46B 9/06*     (2006.01)
    *A46B 15/00*     (2006.01)
    *A46D 1/00*     (2006.01)
    *A61C 17/22*     (2006.01)
    *A61H 13/00*     (2006.01)
    *A61C 17/34*     (2006.01)
    *A61N 5/067*     (2006.01)

(52) U.S. Cl.
    CPC   *A61N 2005/0606* (2013.01); *A61N 2005/063* (2013.01); *A61N 2005/0644* (2013.01); *A61N 2005/0652* (2013.01); *A61N 2005/0662* (2013.01); *A61N 5/067* (2021.08)

(56) References Cited

U.S. PATENT DOCUMENTS

| | | | |
|---|---|---|---|
| 7,942,667 B2 * | 5/2011 | Rizoiu | A46B 15/0002 433/29 |
| 2005/0271997 A1 | 12/2005 | Mikami et al. | |
| 2006/0183071 A1 | 8/2006 | Hsueh | |
| 2007/0271714 A1 * | 11/2007 | Adam | A61N 5/0603 30/32 |
| 2008/0286713 A1 | 11/2008 | Nanda | |
| 2009/0083924 A1 | 4/2009 | Shepherd et al. | |
| 2011/0047729 A1 | 3/2011 | Wahori et al. | |
| 2013/0117950 A1 * | 5/2013 | Kim | A61N 5/06 15/105 |

* cited by examiner

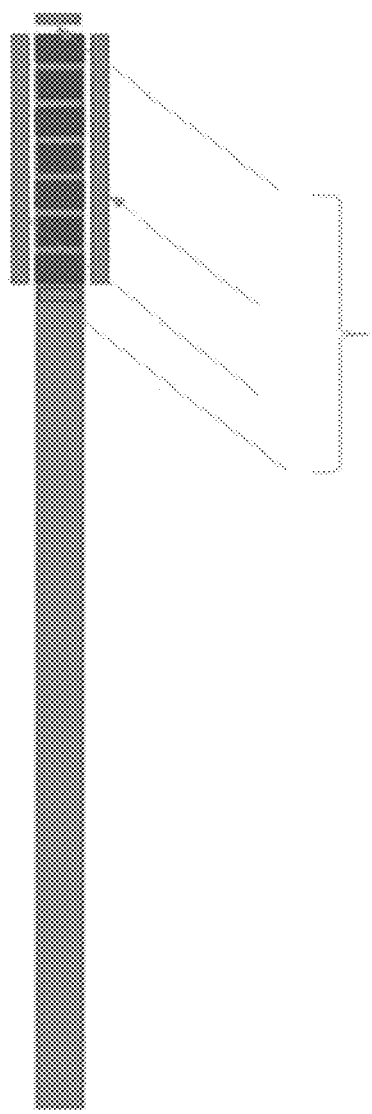
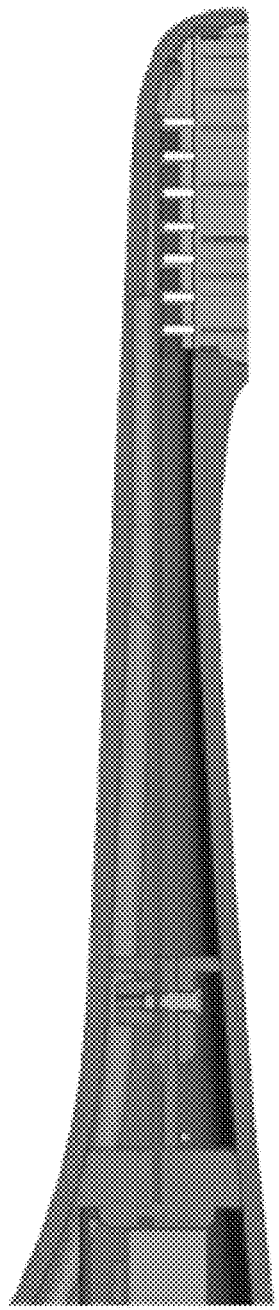
Side wall(s)
FIG. 8A
FIG. 8B

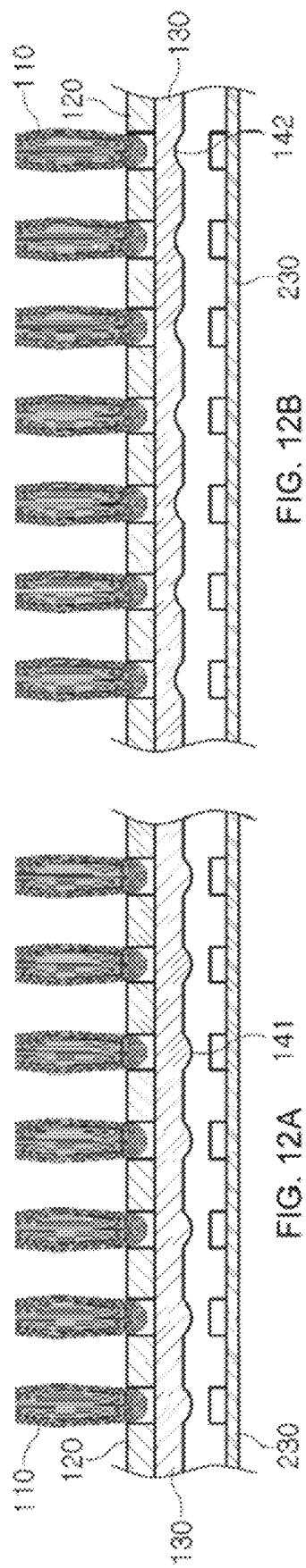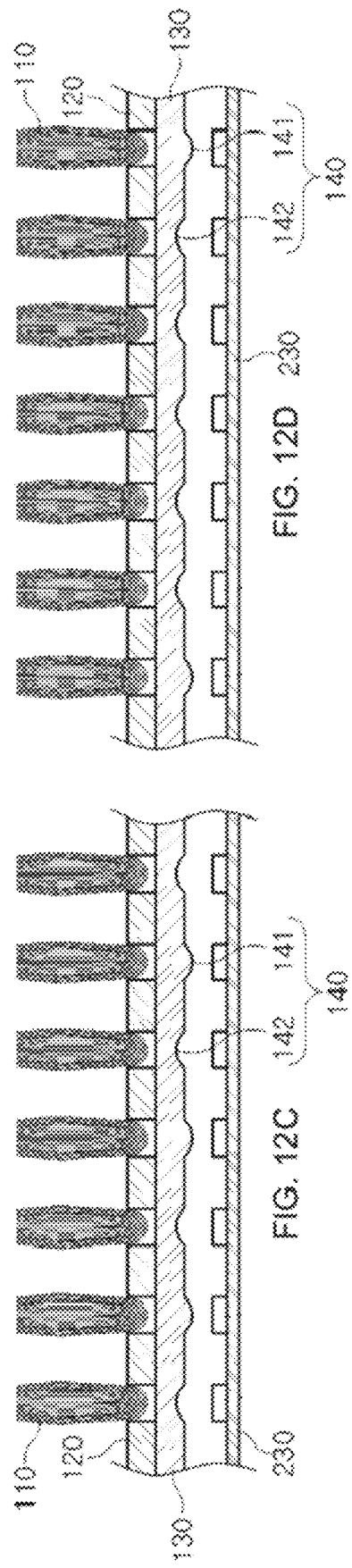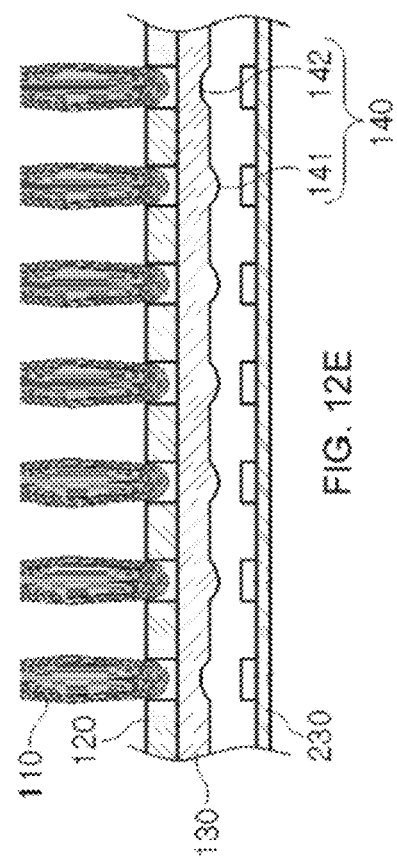

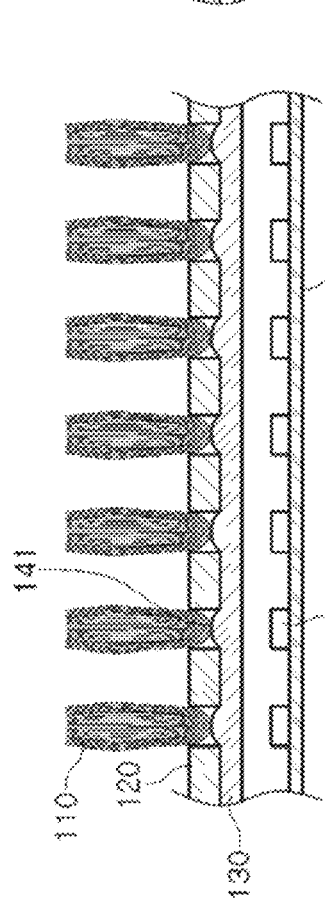
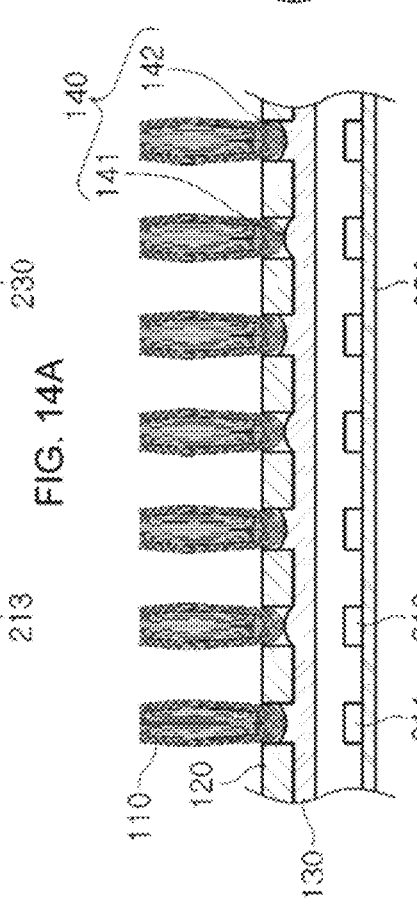
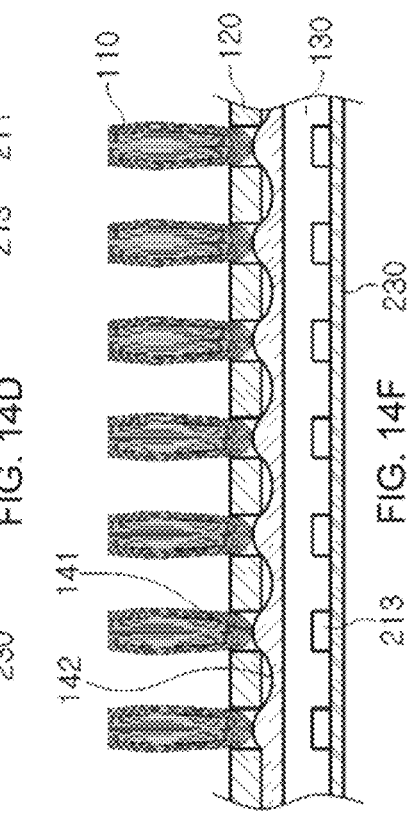
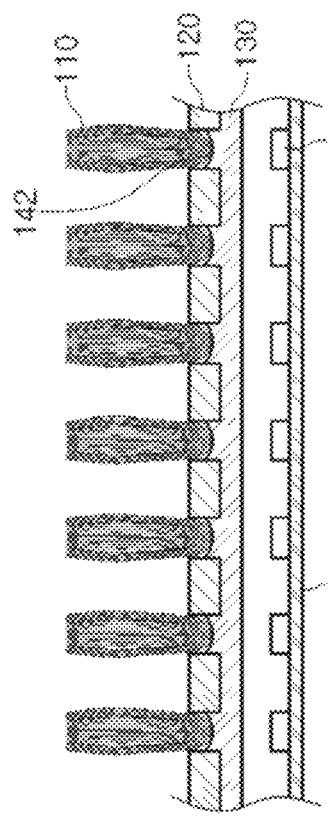
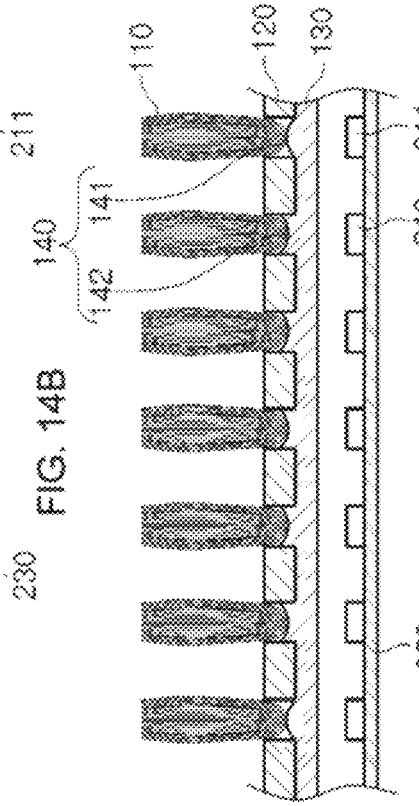

LIGHT IRRADIATING TOOTHBRUSH HAVING MULTIPLE LIGHT SOURCES ARRANGED IN ALTERNATION

CROSS-REFERENCES TO RELATED APPLICATIONS

This application is a continuation-in-part and claims benefit of U.S. patent application Ser. No. 16/400,883, filed May 1, 2019, which is a continuation of U.S. patent application Ser. No. 14/646,397, filed May 21, 2015, which is a 371 application of International Patent Application No. PCT/KR2013/005355, filed Jun. 18, 2013, which claims benefit of K.R. Application No. 10-2012-0132261, filed Nov. 21, 2012.

FIELD OF THE INVENTION

The present invention generally relates to a vibrating toothbrush and, more particularly, to a vibrating toothbrush including light sources for emitting light.

BACKGROUND OF THE INVENTION

As a method of removing oral bacteria that causes plague and tartar to keep teeth sanitary, people generally brush their teeth with a toothbrush or gargle with a liquid containing a chemical antibacterial agent after brushing.

Among various types of toothbrushes, there are vibrating toothbrushes for effectively brushing teeth. Further, since it is difficult to effectively remove bacteria by brushing teeth with common toothbrushes, vibrating toothbrushes that radiate light at a predetermined wavelength band have been proposed.

However, a chemical method using mouthwash is generally used and conventional vibrating toothbrushes using light radiate only white light, so a detailed method of effectively removing oral bacteria has not been proposed yet.

BRIEF SUMMARY OF THE INVENTION

Accordingly, the present invention has been made keeping in mind the above problems occurring in the related art, and the present invention is intended to propose a light irradiating toothbrush that efficiently radiates light into the mouth of a user.

In order to achieve the above object, according to one aspect of the present invention, there is provided a light irradiating toothbrush including a grip and a head operatively coupled to the grip, in which the head includes: brushing bristles made of at least one waveguide; and a light source unit disposed under the brushing bristles inside the head and including a plurality of light sources radiating light through the waveguides, and the light source unit includes a plurality of alternatively arranged light sources radiating light with different wavelengths.

The plurality of light sources may be a set of light sources including a first sub-set that includes at least one first light source radiating short-wavelength light, and a second sub-set that includes at least one second light source radiating long-wavelength light, and the plurality of light sources may be alternatively arranged by repeatedly arranging sets of light sources including the first sub-set and the second sub-set.

The short-wavelength light may be blue light and the long-wavelength light may be red light.

The light sources may be arranged in a longitudinal direction of the head. For example, the longitudinal direction is aligned with the grip and the head.

The light sources may be LEDs (Light-Emitting Diode) or laser diodes.

The light sources may be spaced at different distances from the bristle plate in accordance with the magnitudes of the wavelengths, and a first light source radiating short-wavelength light may be positioned such that the short-wavelength light radiated from the first light source travels a shorter distance to the brushing bristles, as compared with long-wavelength light radiated from a second light source and traveling to the brushing bristles.

The first light source radiating short-wavelength light may be positioned closer to the brushing bristles than the second light source radiating long-wavelength light.

The brushing bristles made of waveguides may be brushing bristles made of optical fibers.

The toothbrush may further include a substrate where the light sources are disposed, and the substrate may have a white color.

The light irradiating toothbrush may further include a vibrating motor, the substrate may be composed of a first substrate and a second substrate, the first substrate may be disposed in the grip, the second substrate may be disposed in the head, the light source unit may be disposed on the second substrate, the vibrating motor may be connected to the second substrate, and the vibrating motor may vibrate the second substrate.

The light irradiating toothbrush may further include a vibration attenuator at a joint of the first substrate and the second substrate and the vibration attenuator may be made of a urethane material.

The head may further include massaging bristles made of waveguides and the massaging bristles may be formed by a bundle of a plurality of waveguides or a plurality of optical fibers.

Both or any one of the brushing bristles and the massaging bristles may be disposed on a bristle plate, and the bristle plate may be detachably attached to the head.

The brushing bristles may be coated with a metallic oxide catalyst or nano-metal, the metallic oxide catalyst may be any one of $TiO_2$, $MnO_2$, and $BaTiO_3$, or a mixture of two or more of them, and the nano-metal may be any one of nano-silver (Ag), nano-white gold (Pt), and nano-gold (Au), or a mixture of two or more of them.

The light irradiating toothbrush may be supplied with power from a battery or through a USB.

According to the light irradiating toothbrush of an embodiment of the present invention, light sources radiating light with different wavelengths are alternately disposed under brushing bristles made of waveguides, so the intensity of light is increased by constructive interference of the light. The heights of the light sources are different in accordance with the wavelength of the light that they radiate so that short-wavelength light is transmitted well to the brushing bristles made of waveguides and light with different wavelengths is transmitted through the brushing bristles made of waveguides. Accordingly, light can be efficiently transmitted into the mouth of a user. Further, since the light irradiating toothbrush according to an embodiment of the present invention further includes a vibrating attenuator, it is possible to reduce the intensity of vibration transmitted from a vibrating motor to the grip.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIG. 8A shows a schematic front view of the light irradiating toothbrush with walls alongside the light source unit according to an embodiment of the present invention.

FIG. 8B shows a side view of the light irradiating toothbrush with walls between the plurality of light sources according to an embodiment of the present invention.

FIG. 12A shows a light source unit of the present invention having a plurality of convex lenses disposed over the plurality of light sources. FIG. 12B shows a light source unit of the present invention having a plurality of concave lenses disposed over the plurality of light sources. FIGS. 12O-12E shows a light source unit of the present invention having a plurality of convex lenses and a plurality of concave lenses disposed over the plurality of light sources.

Figure 13A:
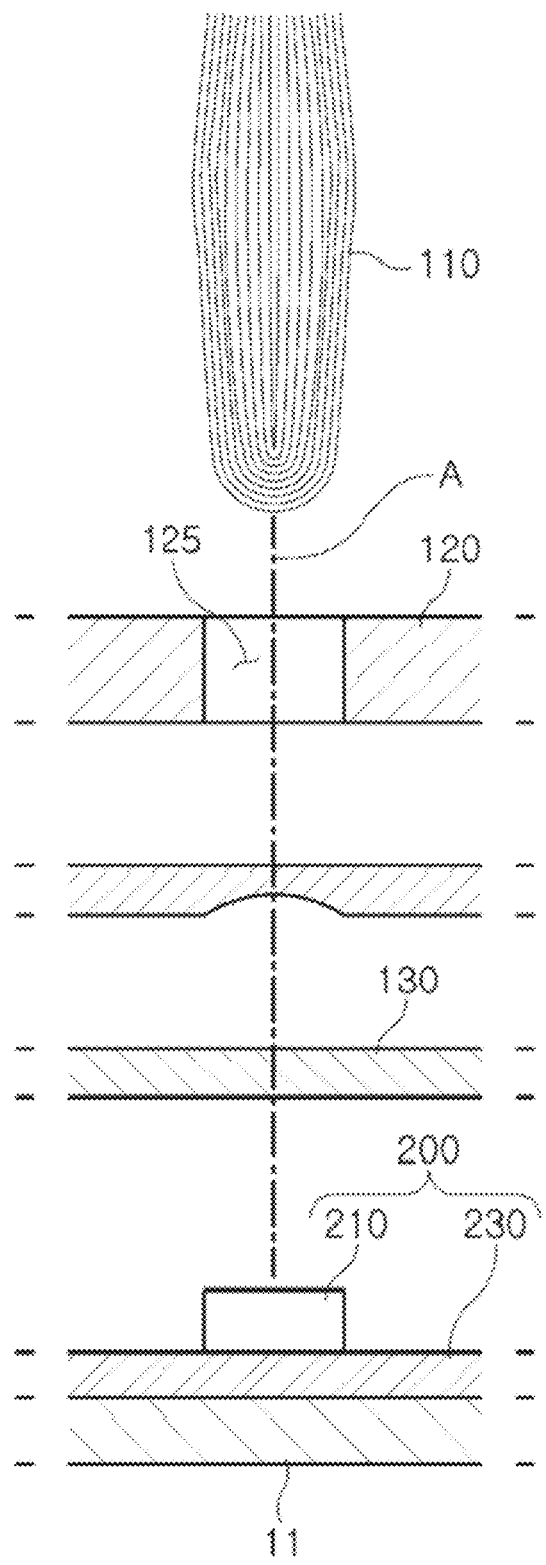
Figure 13B:
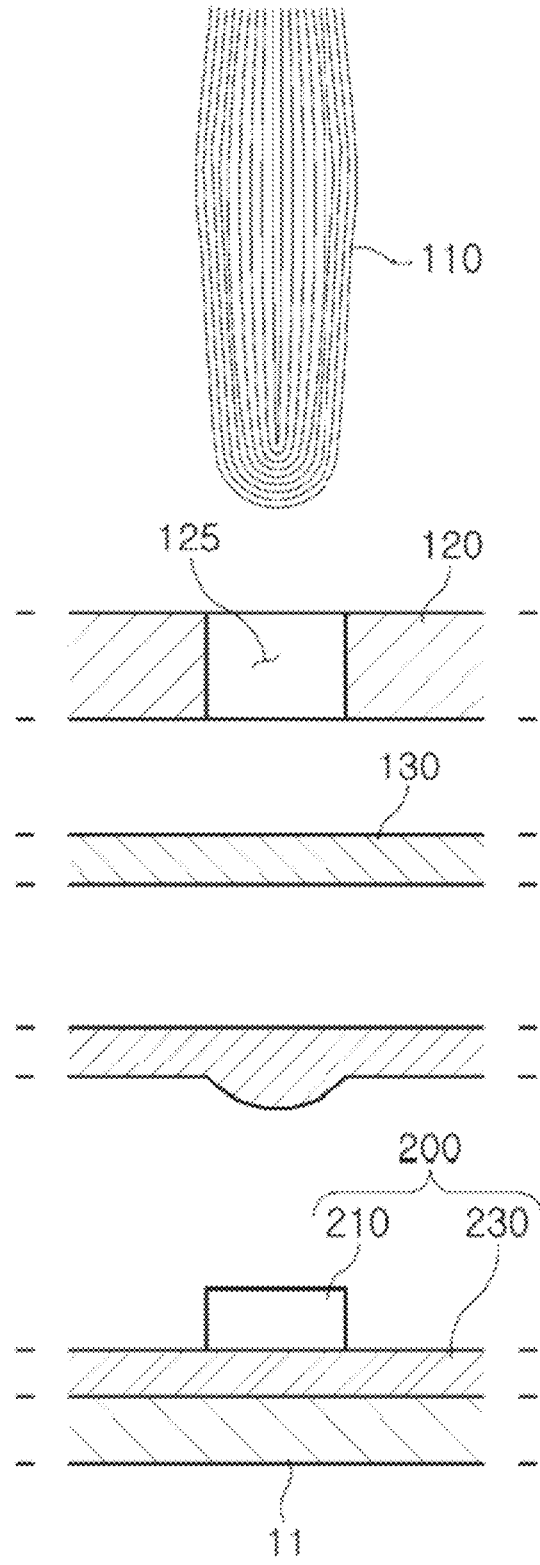
Figure 13C:
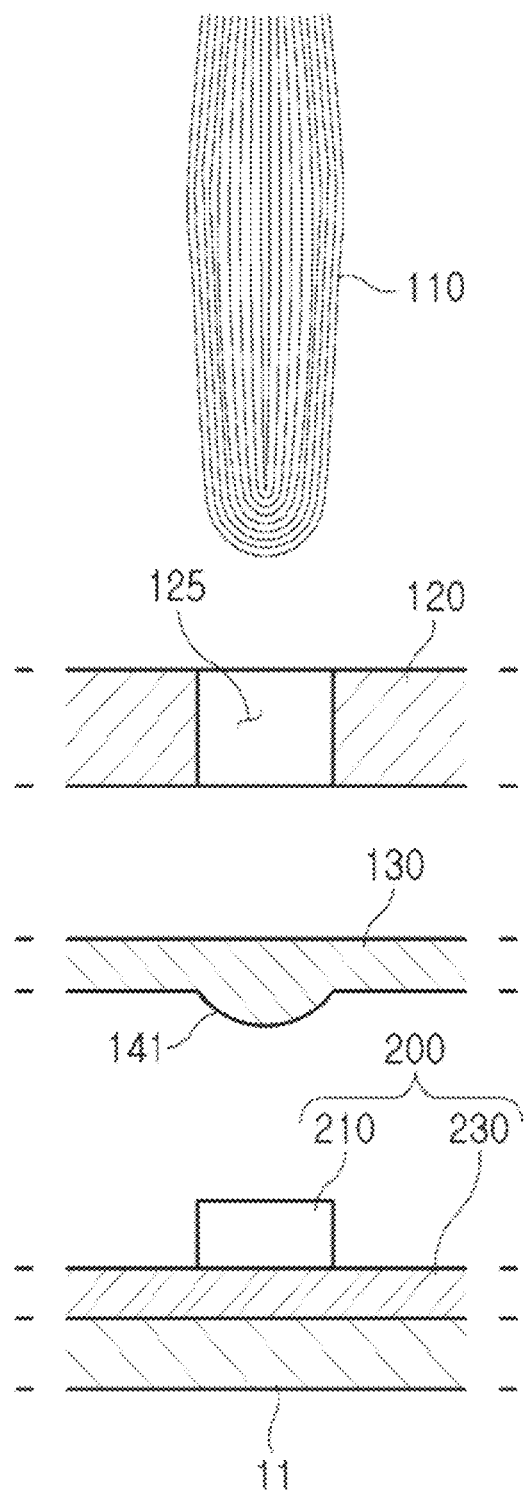
Figure 13D:
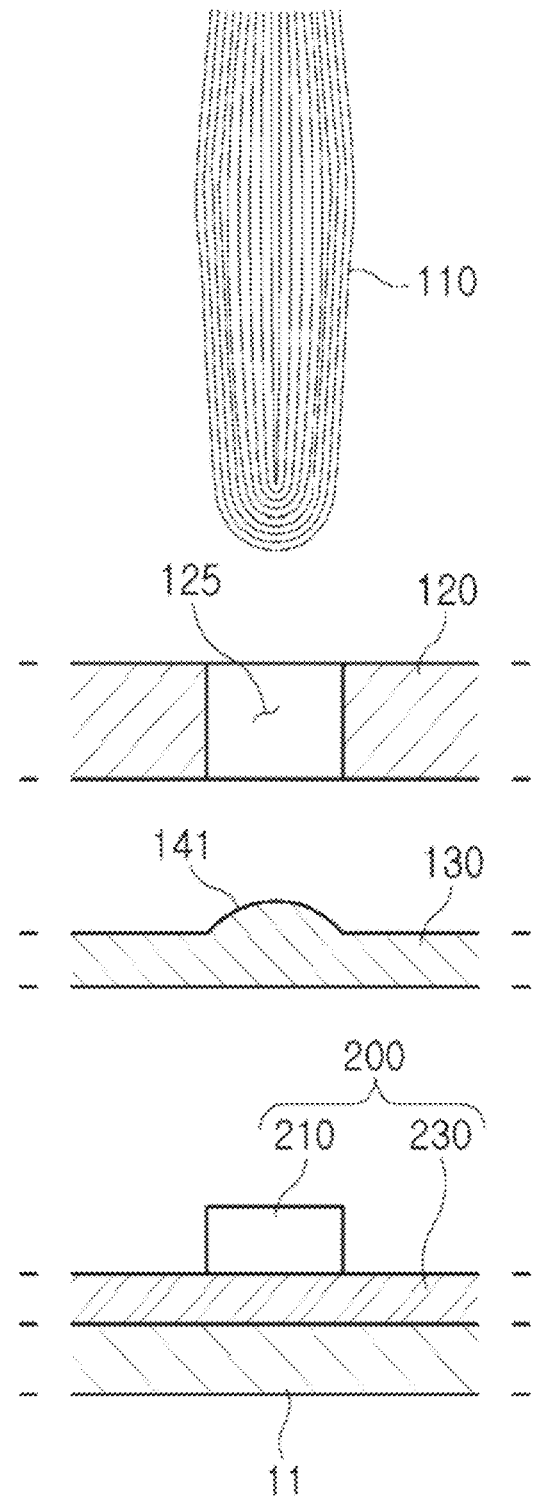
Figure 13E:
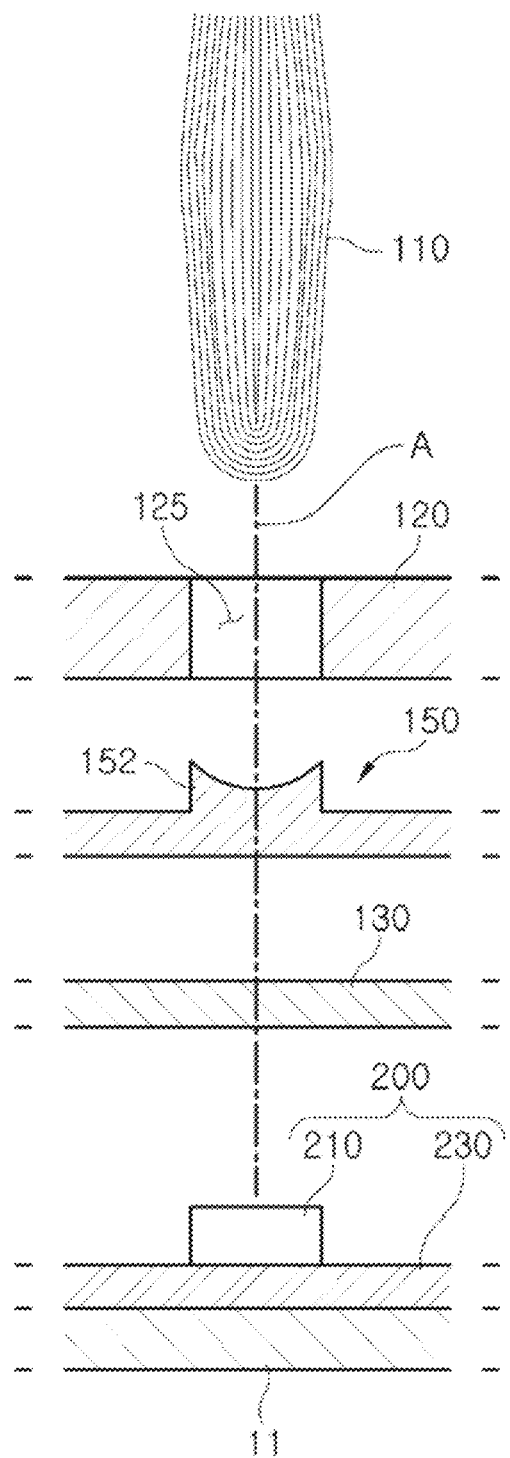
Figure 13F:
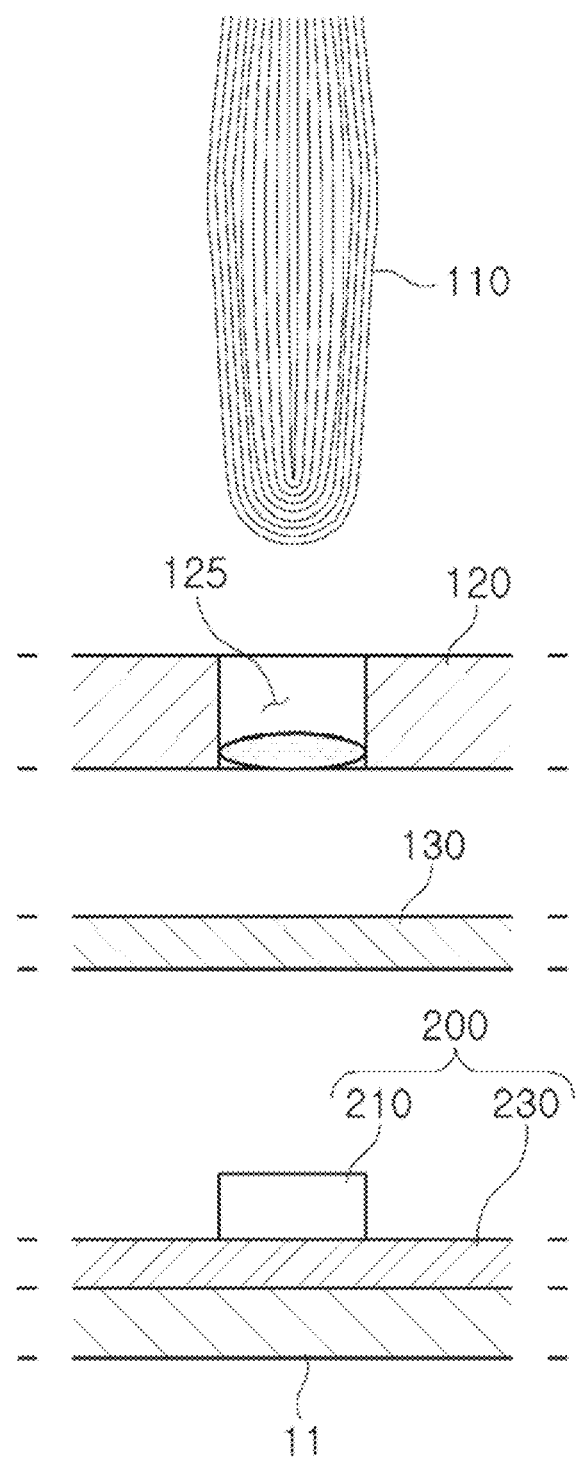

FIG. 13A shows an exploded view of the light source unit transmitting light through a waterproof plate and a concave lens to the toothbrush head. FIG. 13B shows an exploded view of the light source unit transmitting light through a convex lens and a waterproof plate to the toothbrush head. FIG. 13C shows an exploded view of the light source unit transmitting light through a convex lens disposed in a waterproof plate to the toothbrush head, FIG. 13D shows an exploded view of the light source unit transmitting light through a convex lens disposed on an upper surface of the waterproof plate to the toothbrush head. FIG. 13E shows an exploded view of the light source unit transmitting light through a concave lens disposed on the upper surface of the waterproof plate to the toothbrush head. FIG. 13F shows an exploded view of the light source unit transmitting light through a lens to the toothbrush head. Note that A represents the optical axis.

FIG. 14A shows a light source unit of the present invention having a plurality of concave lenses disposed on an upper surface of the waterproof plate. FIG. 14B shows a light source unit of the present invention having a plurality of convex lenses disposed on an upper surface of the waterproof plate. FIGS. 14C-14F shows a light source unit of the present invention having a plurality of convex lenses and a plurality of concave lenses disposed on an upper surface of the waterproof plate.

Figure 15:
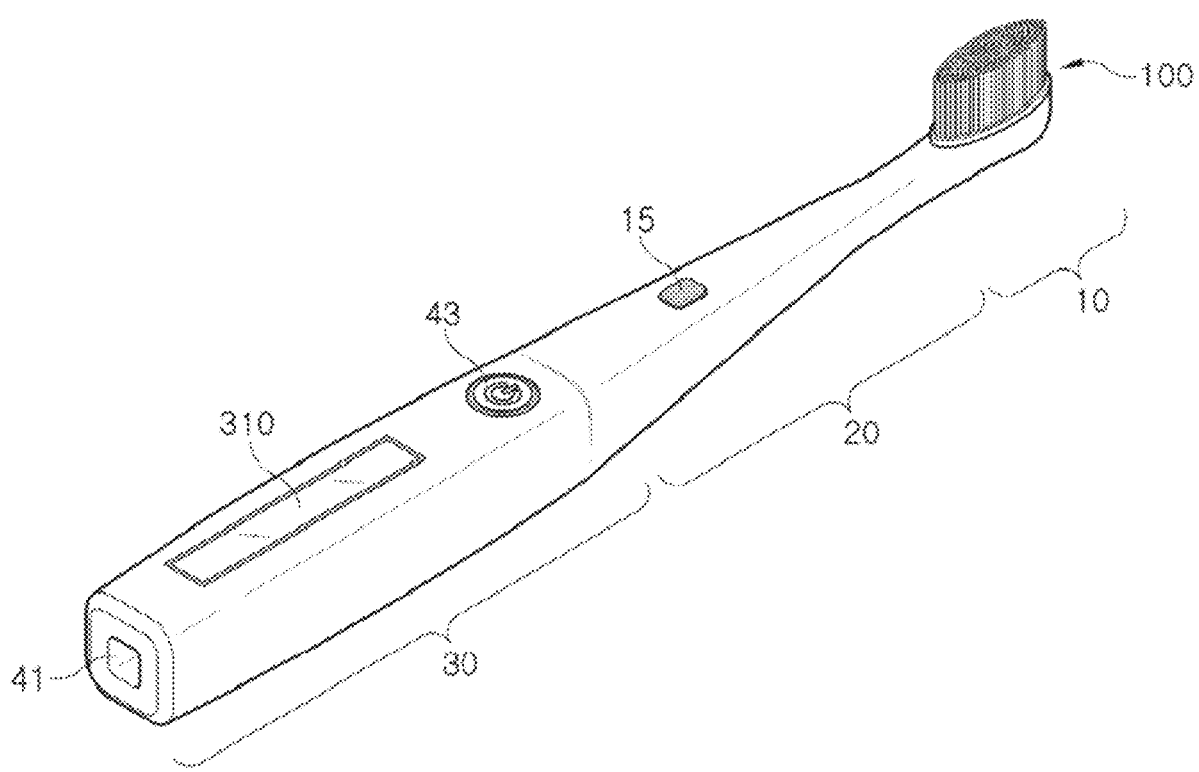

FIG. 15 shows an embodiment of the light irradiating toothbrush of the present invention having a health information display component.

Figure 16A:
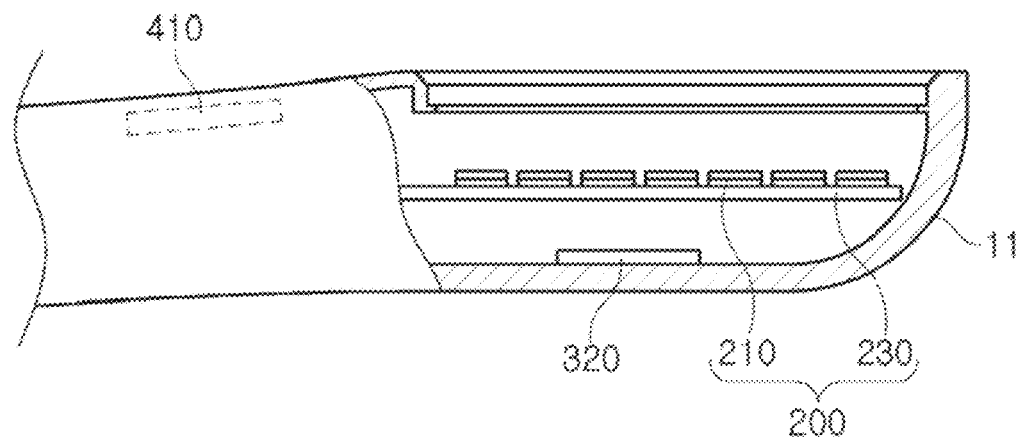
Figure 16B:
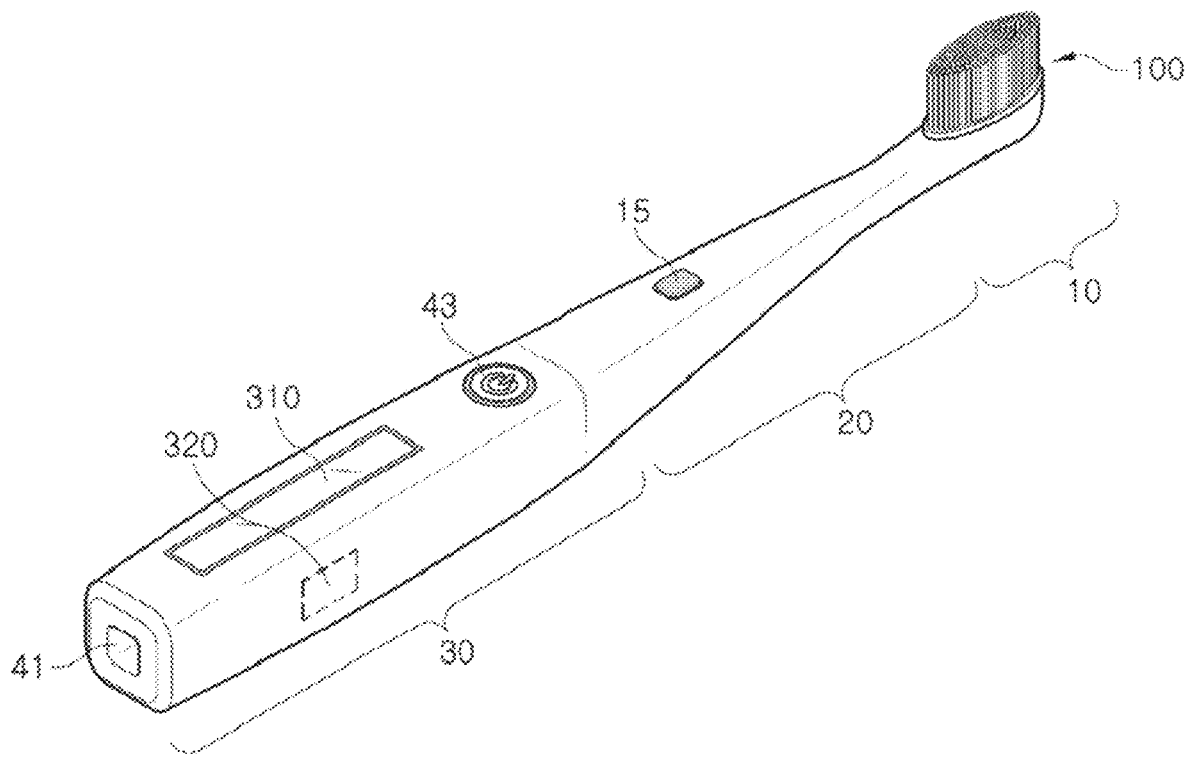

FIG. 16A shows the light irradiating toothbrush of the present invention having one or more health information sensors disposed in the head. FIG. 16B shows the light irradiating toothbrush of the present invention having one or more health information sensors disposed in the grip.

DETAILED DESCRIPTION OF THE INVENTION

The present invention may be modified in various ways by various embodiments, and the embodiments provided are merely examples for describing the present invention in detail.

The present invention, however, is not limited to the embodiments and should be construed as including all of modifications and equivalents within the spirit and scope of the present invention.

Terms used in the specification, 'first', 'second', etc., may be used to describe various components, but the components are not to be construed as being limited to the terms. The terms are used to distinguish one component from another component. For example, the 'first' component may be named the 'second' component, and vice versa, without departing from the scope of the present invention. The term 'and/or' includes a combination of a plurality of items or any one of a plurality of terms.

It is to be understood that when one element is referred to as being "connected to" or "coupled to" another element, it may be connected directly to or coupled directly to another element or be connected to or coupled to another element, having the other element intervening therebetween. On the other hand, it is to be understood that when one element is referred to as being "connected directly to" or "coupled directly to" another element, it may be connected to or coupled to another element without the other element intervening therebetween.

Terms used in the present specification are used only in order to describe specific exemplary embodiments rather than limiting the present invention. As used herein, the singular forms are intended to include the plural forms as well, unless the context clearly indicates otherwise. It will be further understood that the terms "comprises" or "have" used in this specification, specify the presence of stated features, numerals, steps, operations, components, parts, or a combination thereof, but do not preclude the presence or addition of one or more other features, numerals, steps, operations, components, parts, or a combination thereof.

Unless indicated otherwise, it is to be understood that all the terms used in the specification including technical and scientific terms have the same meaning as those that are understood by those who are skilled in the art. It must be understood that the terms defined by a dictionary are identical with the meanings within the context of the related art, and they should not be ideally or excessively formally defined unless the context clearly dictates otherwise.

Figure 1:
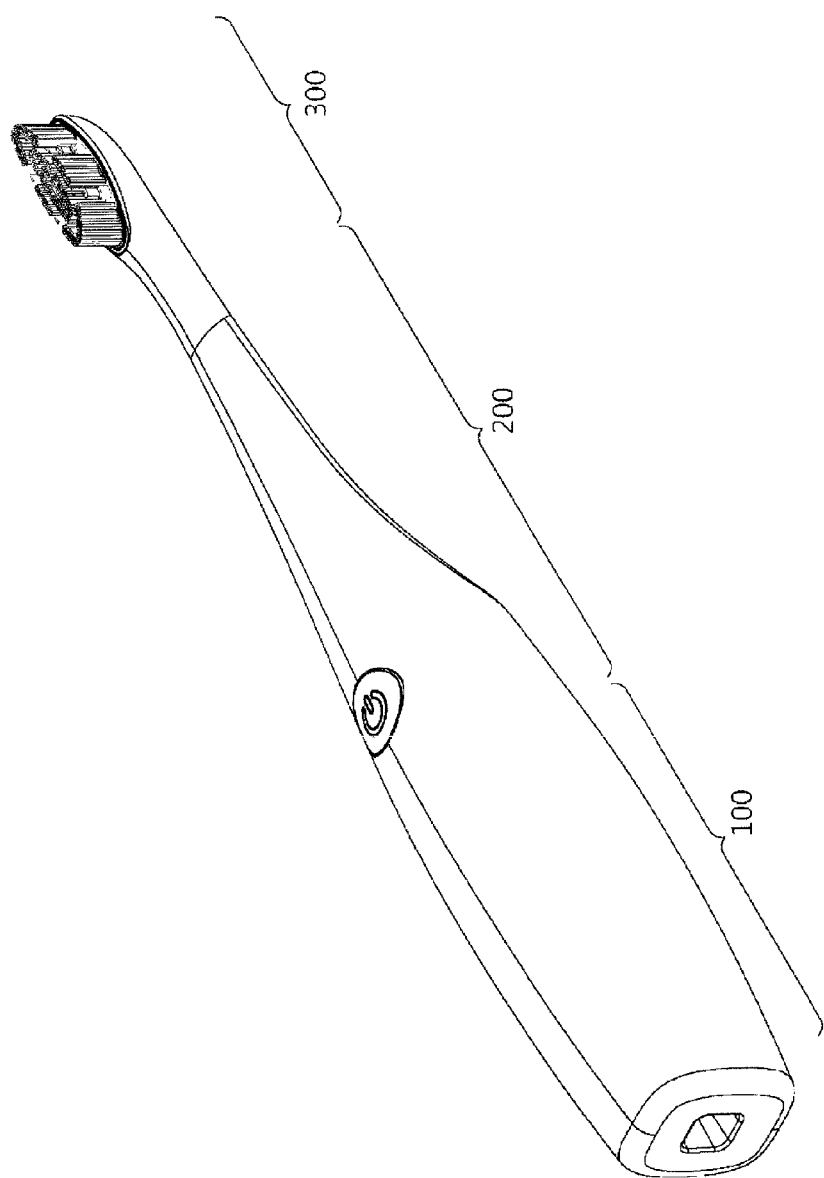
FIG. 1 is a perspective view showing the external shape of a light irradiating toothbrush according to an embodiment of the present invention.

FIG. 1 is a perspective view showing the external shape of a light irradiating toothbrush according to an embodiment of the present invention. The light irradiating toothbrush according to an embodiment of the present invention has a grip 100, a shank 200, and a head 300. The grip 100, which is the part that a user holds, includes a power button 413. The head 300 includes brushing bristles 310 and massaging bristles that are waveguides, and a light source unit 320, and light from light sources is transmitted to the teeth or gums of a user through the brushing bristles 310. The shank 200 connects the grip 100 and the head 300 to each other.

Figure 2:
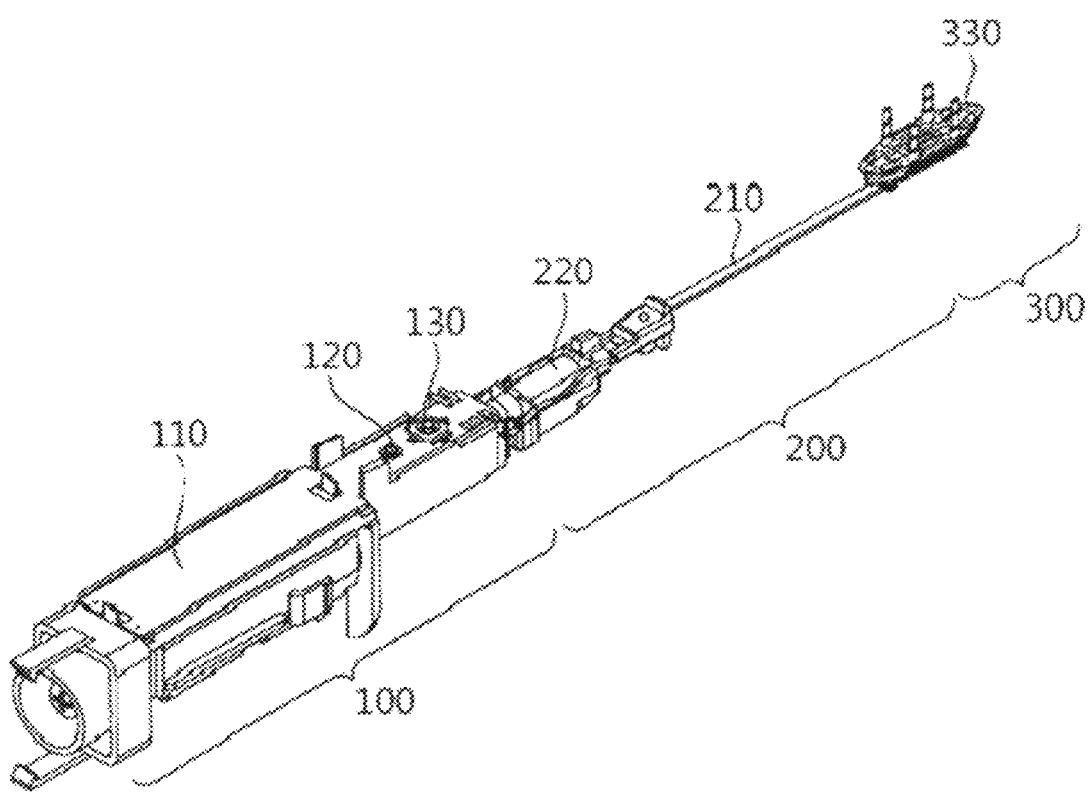
FIG. 2 is a perspective view showing the internal structure of the light irradiating toothbrush according to an embodiment of the present invention.

FIG. 2 is a perspective view showing the internal structure of the light irradiating toothbrush according to an embodiment of the present invention. The internal structure of the light irradiating toothbrush according to an embodiment of the present invention is described with reference to FIG. 2. The grip 100 includes a first substrate 110, a first housing, a power unit (not shown), an operation light 120, and a power switch 130. The shank 200 includes an electric motor, a second substrate 210, a second housing 240, and a vibration attenuator 230. The head 300 includes the brushing bristles 310, the massaging bristles 311, the bristle plate 330, and the light source unit 320 connected to the second substrate 210.

The first substrate and the first housing may be combined. The first housing and the second housing 240 may be combined through a coupler and the coupler may be the vibration attenuator 230. A vibrating motor 220 is disposed inside the second housing 240 and the second housing 240 is connected to the second substrate 210. The light source unit 320 is on an end portion of the second substrate 210. The inside of the light irradiating toothbrush according to an embodiment of the present invention is disposed in a body 500.

The configuration of the grip 100 is described. The power unit supplies power to the light irradiating toothbrush according to an embodiment of the present invention. The power unit supplies power to the vibrating motor 220 and the light source unit 320. The power unit may be disposed inside a space defined by the first substrate 110 and the first housing. Further, the grip 100 may include a controller (not shown) to control the light irradiating toothbrush according to an embodiment of the present invention and the controller may also be disposed in the space defined by the first substrate 110 and the first housing. The controller may be disposed on the first substrate 110. The controller may be capable of generating different levels and patterns of electric current and voltage that affect the performances of the vibration motor and the LEDs (light intensity, wavelength(s) of the light, combination of the wavelengths of the lights).

The first substrate 110 may further include the operation light 120 that indicates operation of the light irradiating toothbrush according to an embodiment of the present invention and the power switch 130 that allows a user to operate the light irradiating toothbrush according to an embodiment of the present invention.

The configuration of the shank 200 is described. The vibrating motor 220 vibrates the light irradiating toothbrush according to an embodiment of the present invention so that the light irradiating toothbrush according to an embodiment of the present invention can work as a vibrating toothbrush. The vibrating motor 220 will be described in detail below.

Figure 3:
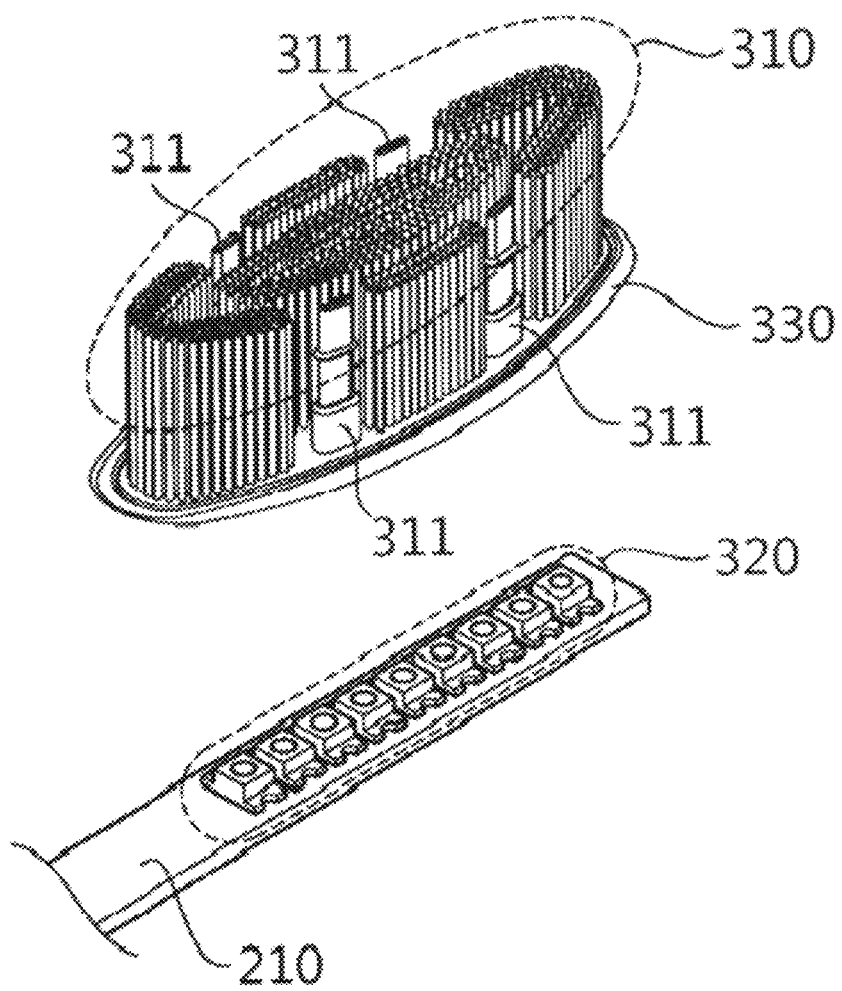
FIG. 3 is a view showing the positional relationship of brushing bristles, massaging bristles, bristle plate, and a light source unit on the head of the light irradiating toothbrush according to an embodiment of the present invention.
Figure 4:
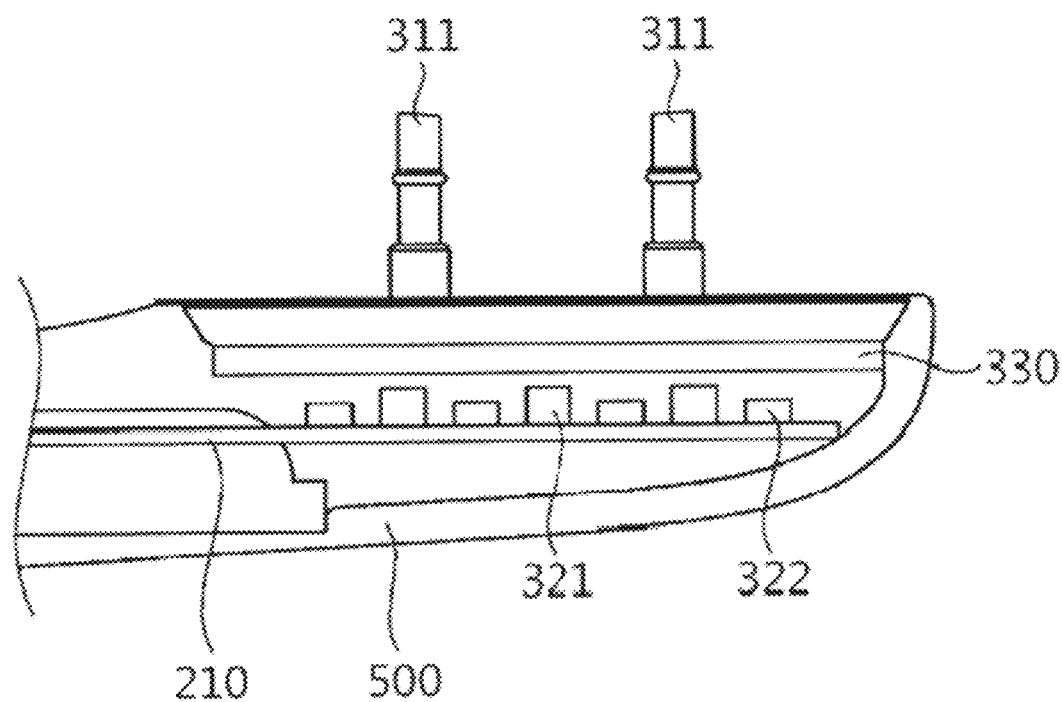
FIG. 4 is a front view showing a case when the bristle plate and the light source unit on the head are combined with the body of the light irradiating toothbrush according to an embodiment of the present invention.
Figure 5:
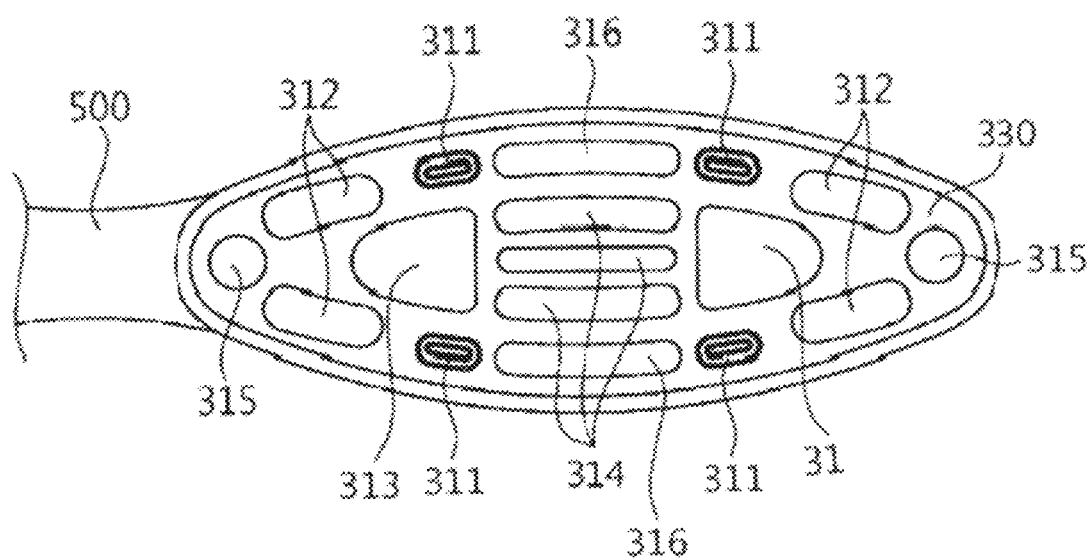
FIG. 5 is a plan view showing a case when the bristle plate on the head is combined with the body of the light irradiating toothbrush according to an embodiment of the present invention.

FIG. 3 is a view showing the positional relationship of the brushing bristles 310, the massaging bristles 311, the bristle plate 330, and the light source unit 320 on the head. FIG. 4 is a front view showing a case when the bristle plate 330 and the light source unit 320 on the head 300 are combined with the body 500 of the light irradiating toothbrush according to an embodiment of the present invention. FIG. 5 is a plan view showing a case when the bristle plate 330 on the head 300 is combined with the body 500 of the light irradiating toothbrush according to an embodiment of the present invention. In other embodiments, the bristle plate 330 is separate from the head 300.

Hereinafter, the configuration of the head of the light irradiating toothbrush according to an embodiment of the present invention is described with reference to FIGS. 3-5.

The brushing bristles 310 include at least one waveguide and transmit light from light sources to the outside. The waveguide means a pipe that transmits light from a light source. The brushing bristle 310 can transmit light from a light source to a tooth of a user. The brushing bristles 310 using a waveguide can be made of an optical fiber.

One or more of the brushing bristles 310 may be coated with a metallic oxide catalyst or nano-metal. Coating with a metallic oxide catalyst and nano-metal is made by spraying them to the brushing bristles 310 or dipping the bristles therein. The metallic oxide catalyst is coated on the brushing bristles 310, using an alcohol liquid with a dispersed metallic oxide, and the nano-metal is coated on the brushing bristles 310, using a nitric acid nano-metal solution.

In some cases, the metallic oxide catalyst and the nano-metal both may be used, in which the brushing bristles 310 are coated with a mixture of an alcohol liquid containing dispersed metallic oxide with the nitric act nano-metal solution.

The metallic oxide catalyst may be any one of $TiO_2$, $MnO_2$, and $BaTiO_2$, or a mixture of two of them, and basically, it has a function of dissolving organic matters. In particular, $TiO_2$ is excellent in dissolution of organic matters and antibacterial function, and $MnO_2$ is known as being excellent in deodorization.

The nano-metal may be any one of nano-silver (Ag), nano-copper (Cu,), nano-white gold (Pt), and nano-gold (Au), or a mixture of two of them. The nano-metals have different functions and may be mixed for use purposes. The nano-metals generally have an antibacterial function, and particularly, nano-silver (Ag) and nano-copper (Cu) have an excellent anti-mold ability in comparison with other nano-metals, so the brushing bristles do not need sterilization.

One or more of the massaging bristles 311 may also be made of waveguides. The massaging bristles 311, which are used to massage the gums of a user, can transmit light from light sources and massage the gums, the inside of the cheek, or the tongue of the user. The massaging bristles 311 may be a bundle of optical fibers for transmitting light well. Alternatively, a bundle of optical fibers cannot have a diameter over a predetermined value, so the brushing bristles 311 may be manufactured by making a bundle of optical fiber in a set and inserting the bundle of optical fiber in the capsules of the brushing bristles 311. Similarly, the massaging bristles 311 may be manufactured by inserting a bundle of waveguides in the massaging bristles 311. The capsules of the massaging bristles 311 receive a bundle of optical fibers or a bundle of waveguides and may be made of a material that transmits light in order to transmit light traveling through the bundle of optical fibers or the bundle of waveguides to gums, etc.

The capsules 311 of the massaging bristles 311 may be covered with a bundle of optical fibers or a bundle of waveguides on the bristle plate 300 to form the massaging bristles 311. The massaging bristles 311 may be disposed on an outer perimeter of the bristle plate 330 or the head 300.

One or both of the brushing bristles 310 and the massaging bristles 311 are disposed on the bristle plate 330 and a stepped portion may be formed at the bristle plate 330 so that the bristle plate can be detached from the head 300 of the body 500 for replacement. The bristle plate 330 may be made of a material that transmits light to transmit light from light sources to the outside.

Arrangement of the brushing bristles 310 is described with reference to FIG. 5. In the brushing bristles 310, 315 at both longitudinal end portions of the bristle plate are longer than the other brushing bristles 3112, 313, 314, and 316 to transmit light well to back teeth. Alternatively, only one of the brushing bristles 315 at an end portion of the toothbrush may be made longest. The brushing bristles 312, 313, 314, and 316 may be arranged to correspond to the arrangement of light sources. The massaging bristles 311 may be arranged at the corners of a virtual rectangle formed around the center of the elliptical bristle plate 330 to massage gums.

The light source unit 320 includes at least one light source. The light source may be a light-emitting element such as an LED or a laser diode. The light sources radiate light with a specific wavelength. The light sources can radiate particularly blue or red light. The light sources can sterilize the inside of a user's mouth or bleach the teeth of a user. Alternatively, the light sources can achieve an anti-inflammatory effect and stimulate collagen formation by radiating red light.

The light sources may be disposed on the second substrate 210. The second substrate 210 may be white to effectively reflect the light from the light sources to the brushing bristles 310. Additionally, the second substrate 210 may comprise a reflective material to further reflect the light from the light sources to the brushing bristles 310. Light sources that radiate light with different wavelengths may be disposed on the second substrate 210. The light sources that radiate light with different wavelengths may be alternately arranged on the second substrate 210. For example, as shown in FIG. 4, sets composed of a first light source 321 that is a blue light source and a second light source 322 that is a red light source may be alternatively arranged on the second substrate 210. The first light source 321 may be a blue light source and the second light source 322 may be a red light source. Sets of a sub-set having a plurality of blue light sources and a sub-set having a plurality of red light sources may be alternately arranged on the second substrate 210. The sub-sets may have the same number of light sources. Alternatively, it may be possible to make green light, white light, or light with other wavelengths by adding a blue or red light source, and it may be possible to generate a high frequency using a high-frequency generator. The light sources may be arranged in a longitudinal direction of the second substrate 210. In other embodiments, the light sources may be arranged in a grid under the bristle plate 330 or in the latitudinal direction of the second substrate 210. When a plurality of light sources is alternately arranged, the intensity of light can be improved by constructive interference of the light.

The light sources may be different in height, depending on the properties of the light that they radiate. This is described with reference to FIG. 4. The first light sources 321 and the second light sources 322 are alternately arranged on the second substrate 210. The first light source 321 may radiate light with a short wavelength, and in an embodiment, the light with a short wavelength may be blue light. The second light source 322 may radiate light with a long wavelength, and in an embodiment, the light with a long wavelength may be red light.

Considering that short-wavelength light disperses more than long-wavelength light, the first light sources 321 radiating short-wavelength light may be positioned closer to the brushing bristles 310 than the second light sources 322 radiating long-wavelength light so that the short-wavelength light travels a shorter distance to objects such as teeth or gums of a user, as compared with the long-wavelength light. The positions of the light sources may depend on the magnitudes of the wavelengths. The distances that the short-wavelength light and the long-wavelength light travel may be different in cases, so the positions of the light sources may be changed in accordance with the detailed configuration of the light irradiating toothbrush according to an embodiment of the present invention.

In more detail, in order to position the first light sources such that the short-wavelength light radiated from the first light sources travels a shorter distance to the brushing bristles, as compared with the long-wavelength light radiated from the second light sources and traveling to the brushing bristles, the first light sources radiating short-wavelength light may be positioned closer to the brushing bristles more than the second light sources radiating long-wavelength light, which can be achieved by making the first light sources higher than the second light sources. This means that the first light sources can be positioned closer to the brushing bristles than the second light sources on the second substrate. Accordingly, the first light sources can be higher than the second light sources. In some embodiments, the first light sources may be manufactured to be taller than the second light sources.

Figure 6:
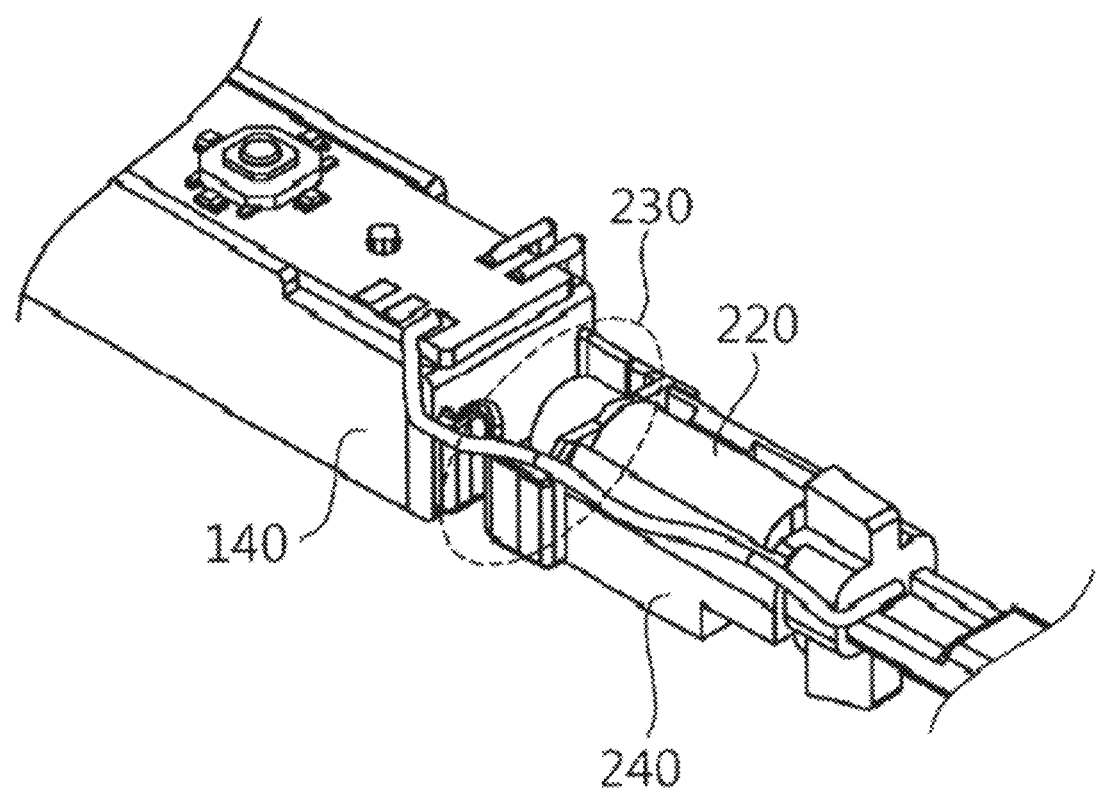
FIG. 6 is a perspective view showing the internal structure of a shank of the light irradiating toothbrush according to an embodiment of the present invention.

FIG. 6 shows the internal structure of the shank 200 of the light irradiating toothbrush according to an embodiment of the present invention. The vibrating motor 220 may be disposed at the grip 100 or the shank 200. In the light irradiating toothbrush according to an embodiment of the present invention, the vibrating motor 220 is disposed at the shank 200. This configuration is described in more detail with reference to FIG. 6. The vibrating motor 220 may be disposed inside the second housing 240.

The vibrating motor 220 applies a physical shock to the second substrate 210, using an elliptical rotor that rotates in the second housing 240, and the second substrate 210 applied a physical shock accordingly to the body 500, so the light irradiating toothbrush according to an embodiment of the present invention can be vibrated. Alternatively, it may be possible to apply a physical shock directly to the second housing 240 using the rotor and make the second housing 240 directly apply a physical shock to the body 500 or transmit vibration to the second substrate to vibrate the light irradiating toothbrush according to an embodiment of the present invention. Alternatively, it may be possible to make the rotor directly apply a physical shock to the body 500 to vibrate the light irradiating toothbrush according to an embodiment of the present invention. The rotor may have the shape of a half-moon or the shape of an elliptical half-moon.

The first housing and the second housing 240 may be combined through the vibration attenuator 320. The vibration attenuator 230 can attenuate the intensity of the vibration that is transmitted from the second housing 240 to the first housing by the vibrating motor 220. The vibration attenuator 230 may be made of a urethane material, silicon, rubber, elastomer, etc.

On the other hand, it is required to supply power to the electric motor, the operation light 120, the power switch 130, and the light source unit 320 in the light irradiating toothbrush according to the present invention, and to this end, the toothbrush may be connected to a home power by a DC adaptor or, when it is carried, it may be supplied with power from a battery or through a USB.

The present invention relates to an electric toothbrush including light sources radiating light and is available for the field of electric toothbrushes that can effectively suppress oral bacteria.

Figure 7:
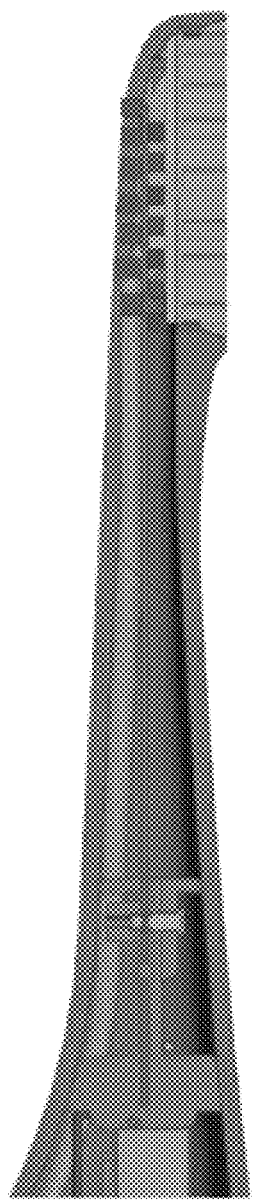
FIG. 7 shows a side view of the light irradiating toothbrush with a back light source according to an embodiment of the present invention.

Referring to FIG. 7, the light irradiating toothbrush may further comprising a back light source unit under the bristle plate inside the head including a plurality of back light sources radiating light to a back of the head of the toothbrush. The back light source unit may include a first back light source radiating short-wavelength light and a second back light source radiating long-wavelength light. The short-wavelength light source and the long-wavelength light source may be disposed at different distances from the bristle plate, in accordance with the magnitude of the wavelengths. The plurality of back light sources may be a set of light sources including a first sub-set that includes at least one first back light source radiating short-wavelength light, and a second sub-set that includes at least one second back light source radiating long-wavelength light. The light sources of the back light source unit may be alternately arranged under the bristle plate to allow for constructive interference of the back light sources. This embodiment may direct light into the mouth of a user in an opposite direction from the light source unit.

Referring to FIGS. 8A-8B, the light irradiating toothbrush may further comprise one or more walls disposed alongside the light source unit (see FIG. 8A) or between the plurality of light sources (see FIG. 8B). Rectangular walls placed alongside the LEDs may harness the light diverging towards the sideways and bounce back the light so that the system channels more photons and guide them to go upwards. The one or more walls may guide the short-wavelength light and the long-wavelength light towards a mouth of a user. The one or more walls may comprise a reflective material such as shiny metal, mirror, shiny material coated glass, or polymer plastic. The one or more walls may be coated with or made of the reflective material.

Figure 9:
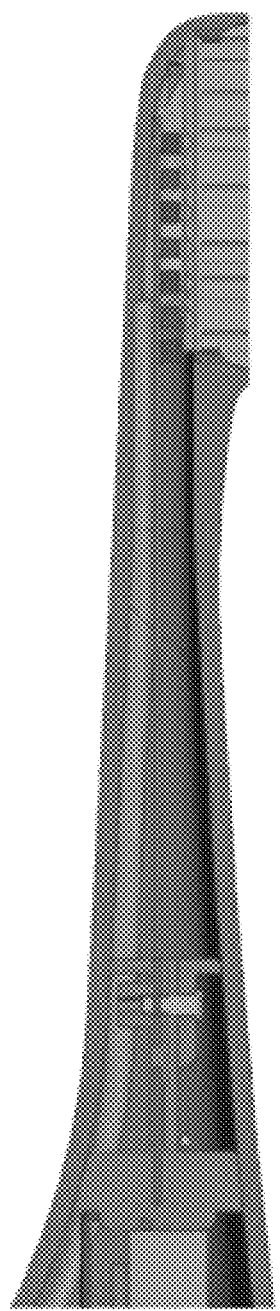
FIG. 9 shows a side view of the light irradiating toothbrush with a plurality of forms disposed above the light source unit according to an embodiment of the present invention.
Figure 10:
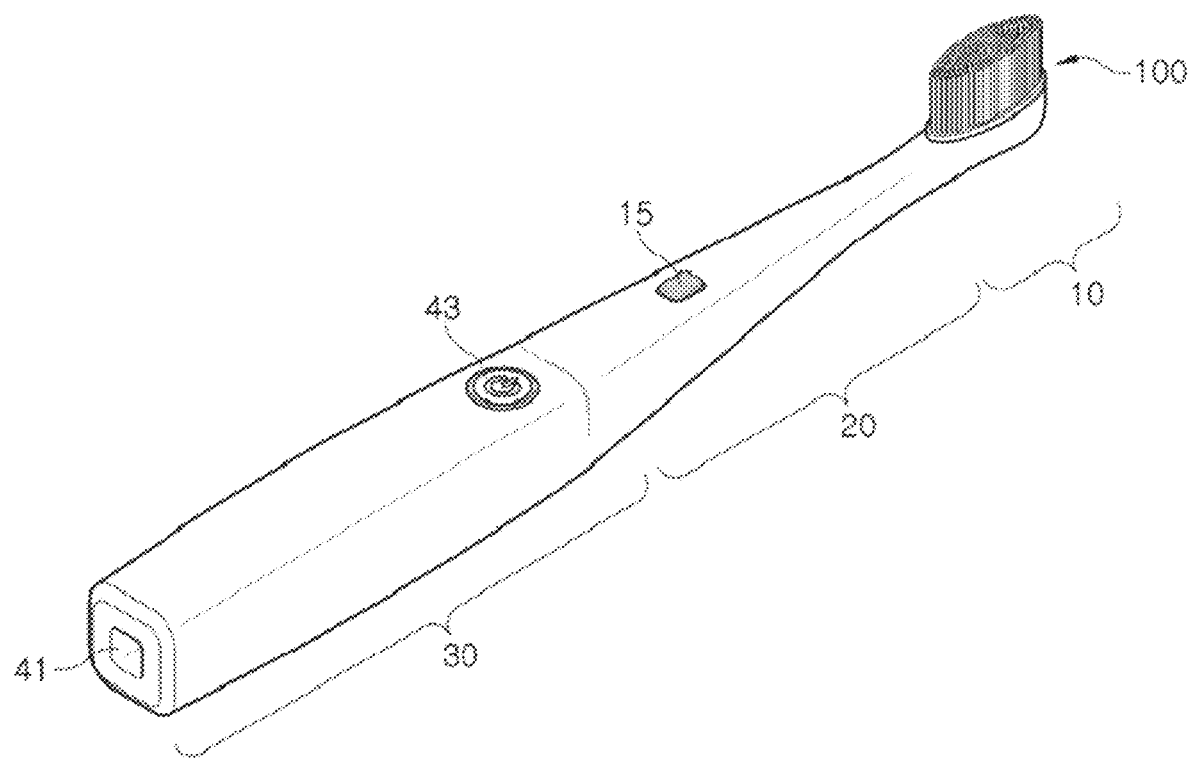
FIG. 10 shows a perspective view showing the external shape of a light irradiating toothbrush according to an alternate embodiment of the present invention comprising a detaching switch allowing the head to detach from the bristle plate.
Figure 11:
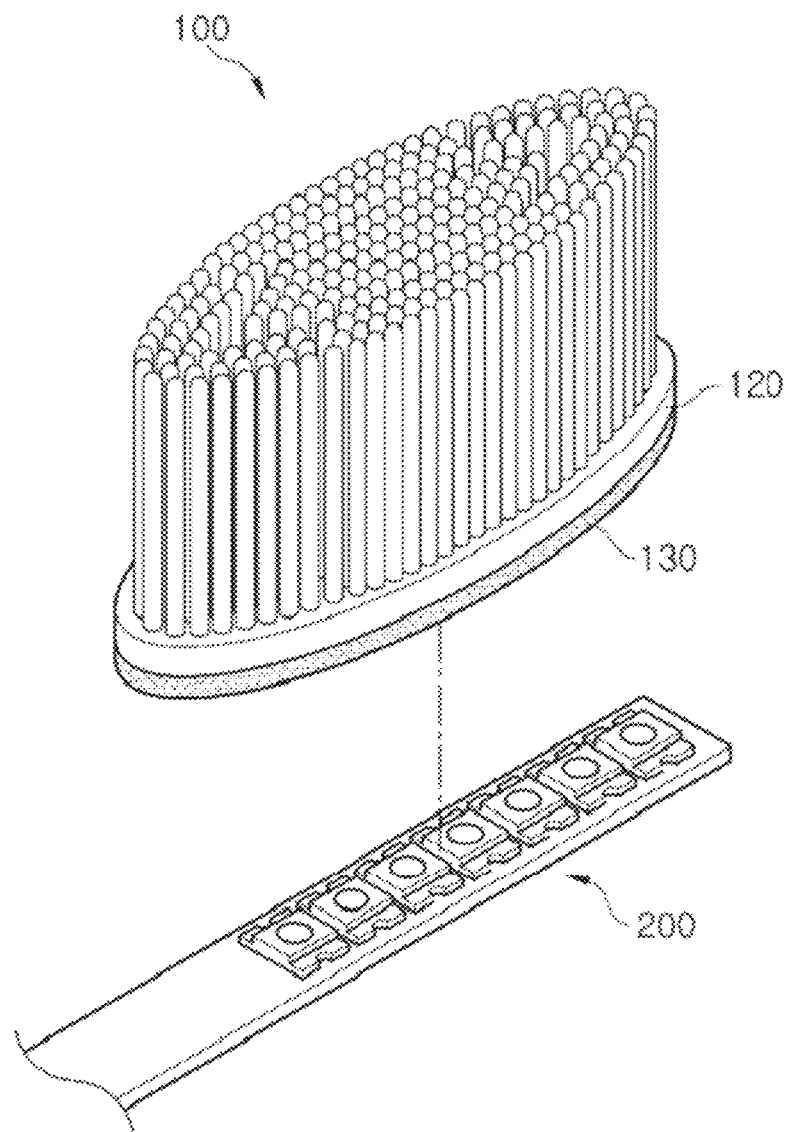
FIG. 11 shows a view showing the positional relationship of the bristle plate, a waterproof plate, and a light source unit on the head of the light irradiating toothbrush according to an embodiment of the present invention.

Referring to FIG. 9, the light source unit comprises a plurality of forms selected from a group consisting of concave dents, convex dents, embossments, or a combination thereof. Each light source of the plurality of light sources may direct light through a form of the plurality of forms. This may result in a lens effect of the light directed through the plurality of forms. The plurality of forms may be made of clear/transparent plastic, plexiglass (IR transmitting plastic).

Referring to FIG. 9, the present invention features a light irradiating toothbrush comprising a grip and a head operatively coupled to the grip. The head may include a detachable bristle plate in which brushing bristles made of at least one waveguide are disposed. The light irradiating toothbrush may further comprise a light source unit disposed under the bristle plate inside the head that includes a plurality of light sources radiating light through the waveguides of the brushing bristles. The light source unit may include a light source comprising a plurality of lights each capable of radiating a plurality of wavelengths of light. The plurality of lights may be a set of lights including a first sub-set that includes at least one first light source radiating a first light, and a second sub-set that includes at least one second light source radiating a second light. The light sources of the light source unit may be alternately arranged under the bristle plate. Each light may be capable of emitting red, green, and blue light in many combinations to achieve any given color. In this embodiment, the light irradiating toothbrush may have voltage/current control to generate different colors.

An embodiment of the present invention for achieving the above object has light transmittance, bristles for cleaning the oral cavity, a bristle support plate having a plurality of bristle insertion holes in which the plurality of bristles are inserted and supported and supporting the bristles partially inserted into the bristles insertion hole, and a waterproof plate that is transparent to light and is coupled to the lower side of the bristle support plate, but an optical means 140 for condensing or dispersing light traveling from the lower side of the waterproof plate to the bristle side is the lower surface of the waterproof plate.

In some embodiments, the optical means 140 may be provided at a position corresponding to the bristle insertion hole on the lower surface of the waterproof plate as another feature. The optical means 140 provided on the lower side or the lower surface of the waterproof plate may be concave in the lower surface of the waterproof plate so that the light incident from the lower side of the waterproof plate is condensed or dispersed and transmitted to the upper surface of the waterproof plate. It may also be characterized as being a concave formed.

In some embodiments, the optical means 140 provided on the lower side or lower surface of the waterproof plate may be convex on the lower surface of the waterproof plate so that the light incident from the lower side of the waterproof plate is condensed or dispersed and transmitted to the upper surface of the waterproof plate. It may also be characterized as a convex-formed plate. Here, a cross-section of at least a portion of the waterproofing plate may be a plano-concave lens, a double-concave lens, a plano-convex lens, a double-convex lens, a positive-meniscus lens, or a negative meniscus lens.

The bristle module according to another embodiment of the present invention for achieving the object as described above may comprise a transmittance to light, bristles for cleaning the oral cavity, and a bristle support plate having a plurality of bristle insertion holes in which the plurality of bristles are inserted to support the bristles partially inserted into the bristles insertion hole. The bristle module may further comprise a waterproof plate coupled to the lower side of the bristle support plate. An optical path controller that comprises the transmittance to light may be provided on the lower side of the waterproof plate, and condense or disperse light traveling toward the waterproof plate or the bristles.

In some embodiments, at least a portion of the optical path controller includes a plano-concave lens, a double-concave lens, a plano-convex lens, a double-convex lens, a positive meniscus lens, or a negative meniscus lens. In some embodiments, in the optical path controller, an optical axis of a portion having any one of a positive meniscus lens and a negative meniscus lens may be formed to pass through the bristle insertion hole.

A sanitary optical toothbrush according to an embodiment of the present invention for achieving the above object may comprise a head unit provided to be drawn into the oral cavity to clean the oral cavity, a connection part connected to one side of the head part to support the head part so that the washing can be performed in the oral cavity, and a handle part connected to one side of the connection part to support the connection part. The head part may comprise a bristle module that is drawn into the oral cavity to contact the tongue, gums or teeth to perform the cleaning and a light source module that emits light passing through the bristle module for cleaning or hygiene in the oral cavity. A power supply device for supplying power may be provided, and the bristle module may be characterized as one of the bristle modules as described above. The light irradiating toothbrush may further comprise a charging port 41 as depicted in FIG. 16B.

In some embodiments, the bristle module may be selectively fastened to or separated from the head part, and the connection part or the handle part may be provided with a bristle module detachable switch so that the bristle module can be separated from the head part.

Furthermore, an ultrasonic wave generating device for generating ultrasonic waves to clean the bristles of the bristle module may be provided in any one of the head part, the connection part, and the handle part as another feature. In some embodiments, a vibrating device for generating vibration so that the bristles of the bristle module vibrate in the oral cavity. The vibrating device may be mounted on any one of the handle part, the connection part, and the head part.

A sanitary optical toothbrush according to another embodiment of the present invention for achieving the above object may comprise a head unit provided to be drawn into the oral cavity to clean the oral cavity, a connection part connected to one side of the head part to support the head part so that the washing can be performed in the oral cavity, and a handle part connected to one side of the connection part to support the connection part. The head part may comprise a bristle module that is drawn into the oral cavity to contact the tongue, gums or teeth to perform the cleaning, a light source module for emitting light passing through the bristle module for cleaning or hygiene in the oral cavity, and an optical controller located between the bristle module and the light source module such that the light emitted from the light source module side while proceeding toward the bristle module is adjusted. The toothbrush may further comprise a power supply device for supplying power to the light source module side of the head part is provided on the handle part.

Here, a cross-section of at least a portion of the optical path controller is a plano-concave lens, a double-concave lens, a plano-convex lens, a double-convex lens, A positive meniscus lens, or a negative meniscus lens shape. In some embodiments, the bristle module may be selectively fastened to or separated from the head part. The connection part or the handle part may be provided with a bristle module separation switch so that the bristle module can be separated from the head part.

In some embodiments, the toothbrush may further comprise an ultrasonic wave generating device for generating ultrasonic waves to dean the bristles of the bristle module and may be disposed in any one of the head, the connection part, or the handle part.

In some embodiments, the toothbrush may further comprise a vibrating device for generating vibrations so that the bristles of the bristle module vibrate in the oral cavity. The vibrating device may be mounted on any one of the handle part, the connection part, and the head part.

In some embodiments, the brushing bristles of the light irradiating toothbrush of the present invention may comprise a transparent material such that the light from the light source unit cleans an oral cavity. In some embodiments, the light irradiating toothbrush may further comprise a bristle support plate having a plurality of bristle insertion holes in which the plurality of bristles are inserted such that the bristle support plate supports the bristles at least partially inserted into the bristle insertion holes. The light irradiating toothbrush may further comprise a waterproof plate coupled to a lower side of the bristle support plate. The light irradiating toothbrush may further comprise an optical means 140 disposed on a lower side of the waterproof plate for condensing or dispersing the light traveling from the lower side of the waterproof plate toward the bristles. In some embodiments, the optical means 140 may comprise a concave lens, a convex lens, a plano-concave lens, a double-concave lens, a plano-convex lens, a double-convex lens, or a combination thereof. In other embodiments, the optical means 140 may comprise a positive-meniscus lens or a negative-meniscus lens, and the bristle support plate and the waterproof plate may match a shape of the optical means 140. In some embodiments, the bristle plate may be detachable from the head. The light irradiating toothbrush may further comprise a detaching switch such that when the detaching switch is actuated, the bristle support plate detaches from the head. The light irradiating toothbrush may further comprise an ultrasonic wave generating device disposed in the head or the grip for generating ultrasonic waves to clean the bristles.

The optical means may comprise one or more lenses of different types (convex, concave, etc.). In some embodiments, the optical means may be disposed on an upper side of the waterproof plate 130. In other embodiments, the optical means 140 may be disposed on a lower side of the waterproof plate 130. The optical means 140 may be aligned to the plurality of bristle insertion holes, or aligned between the plurality of bristle insertion holes. In some embodiments, the light irradiating toothbrush may comprise a light path controller disposed on an upper side of the waterproof plate 130 capable of condensing or dispersing light from the light source unit 200. At least a portion of the light path controller may comprise a lens selected from a group consisting of a concave lens 142, a plano-concave lens, a double-concave lens, a convex lens 141, a plano-convex lens, a double-convex lens, a positive meniscus lens, and a negative meniscus lens. Each bristle insertion hole of the plurality of bristle insertion holes of the bristle support plate may comprise an optical axis portion matching a shape of the lens. In some embodiments, the light irradiating toothbrush may further comprise an ultrasonic wave generating device 410 disposed in the head 10 or the grip 30 for generating ultrasonic waves to clean the bristles.

The light irradiating toothbrush may further comprise one or more health information sensors 320 capable of sensing a heartbeat, pulse, and blood pressure of a user. The light irradiating toothbrush may further comprise a processor disposed in the grip 30, communicatively coupled to the one or more health information sensors 320, capable of executing computer-readable instructions and receiving the heartbeat, pulse, and blood pressure and generating health information of the user. The light irradiating toothbrush may further comprise a health information display 320 communicatively coupled to the processor, disposed on a surface of the grip 30, capable of displaying the health information of the user. In some embodiments, the one or more health information sensors 320 are disposed in the grip 30. In other embodiments, the one or more health information sensors 320 are disposed in the head 10 under the light source unit 200. The one or more health information sensors 320 may comprise a reflectance oximetry sensor. The processor may be further capable of transmitting the health information to a health information department database. The light irradiating toothbrush may further comprise a power supply disposed in the grip 30, operatively coupled to the light source unit 200, the health information display 320, the processor, and the one or more health information sensors 320.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

EMBODIMENTS

The following embodiments are intended to be illustrative only and not to be limiting in any way.

Embodiment 1: A light irradiating toothbrush comprising: a grip; a head operatively coupled to the grip, wherein the head includes a detachable bristle plate in which brushing bristles made of at least one waveguide are disposed; and a light source unit disposed inside the head and under the bristle plate that includes a plurality of light sources radiating light through the waveguides of the brushing bristles, wherein the light source unit includes a first light source radiating short-wavelength light and a second light source radiating long-wavelength light, the short-wavelength light source and the long-wavelength light source being disposed at different distances from the bristle plate, in accordance with the magnitude of the wavelengths, further wherein the plurality of light sources is a set of light sources including a first sub-set that includes at least one first light source radiating short-wavelength light, and a second sub-set that includes at least one second light source radiating long-wavelength light, and the light sources of the light source unit are alternately arranged under the bristle plate.

Embodiment 2: The light irradiating toothbrush of embodiment 1, wherein the short-wavelength light is blue light and the long-wavelength light is red light.

Embodiment 3: The light irradiating toothbrush of embodiment 1, wherein the light sources are arranged in a longitudinal direction of the head.

Embodiment 4: The light irradiating toothbrush of embodiment 1, wherein the light sources are LEDs (Light-Emitting Diode) or laser diodes.

Embodiment 5: The light irradiating toothbrush of embodiment 1, wherein the light source unit includes a first light source radiating short-wavelength light and second light source radiating long-wavelength light, and the first light source is positioned closer to the brushing bristles than the second light source.

Embodiment 6: The light irradiating toothbrush of embodiment 1, wherein the brushing bristles are optical fibers.

Embodiment 7: The light irradiating toothbrush of embodiment 1, wherein the light source unit further includes a substrate on which the light sources are disposed, and the second substrate has a white color.

Embodiment 8: The light irradiating toothbrush of embodiment 1, further comprising a vibrating motor and a substrate on which the light sources are disposed, wherein the substrate comprises a first substrate and a second substrate, the first substrate being disposed in the grip, the second substrate being disposed in the head, the light source unit being disposed on the second substrate, wherein the vibrating motor is connected to the second substrate and vibrates the second substrate.

Embodiment 9: The light irradiating toothbrush of embodiment 8, further comprising a vibration attenuator at a joint of the first substrate and the second substrate.

Embodiment 10: The light irradiating toothbrush of embodiment 1, wherein the bristle plate in the head further includes massaging bristles comprising waveguides.

Embodiment 11: The light irradiating toothbrush of embodiment 10, wherein the massaging bristles are formed by a bundle of a plurality of waveguides or a plurality of optical fibers.

Embodiment 12: The light irradiating toothbrush of embodiment 10, wherein the massaging bristles further include capsules covering the massaging bristles.

Embodiment 13: The light irradiating toothbrush of embodiment 1, wherein the brushing bristles are coated with a metallic oxide catalyst or nano-metal.

Embodiment 14: The light irradiating toothbrush of embodiment 13, wherein the metallic oxide catalyst is any one of TiO2, MnO2, and BaTiO3, or a mixture of two or more of TiO2, MnO2, and BaTiO3.

Embodiment 15: The light irradiating toothbrush of embodiment 13, wherein the nano-metal is any one of nano-silver (Ag), nano-copper (Cu), nano-white gold (Pt), and nano-gold (Au), or a mixture of two of nano-silver (Ag), nano-copper (Cu), nano-white gold (Pt), and nano-gold (Au).

Embodiment 16: The light irradiating toothbrush of embodiment 1 further comprising a back light source unit under the bristle plate inside the head that includes a plurality of back light sources radiating light to a back of the head, wherein the back light source unit includes a first back light source radiating short-wavelength light and a second back light source radiating long-wavelength light, the short-wavelength light source and the long-wavelength light source being disposed at different distances from the back of the head, in accordance with the magnitude of the wavelengths, further wherein the plurality of back light sources is a set of light sources including a first sub-set that includes at least one first back light source radiating short-wavelength light, and a second sub-set that includes at least one second back light source radiating long-wavelength light, and the light sources of the back light source unit are alternately arranged under the bristle plate.

Embodiment 17: The light irradiating toothbrush of embodiment 1 further comprising one or more walls disposed alongside the light source unit or between the plurality of light sources, wherein the one or more walls guide the short-wavelength light and the long-wavelength light towards a mouth of a user.

Embodiment 18: The light irradiating toothbrush of embodiment 17, wherein the one or more walls comprise a reflective material.

Embodiment 19: The light irradiating toothbrush of embodiment 1, wherein the light source unit comprises a plurality of forms selected from a group consisting of concave dents, convex dents, embossments, or a combination thereof, wherein each light source of the plurality of light sources directs light through a form of the plurality of forms.

Embodiment 20: The light irradiating toothbrush of embodiment 1, wherein the brushing bristles comprise a transparent material such that the light from the light source unit cleans an oral cavity.

Embodiment 21: The light irradiating toothbrush of embodiment 1 further comprising a bristle support plate having a plurality of bristle insertion holes in which the plurality of bristles are inserted such that the bristle support plate supports the bristles at least partially inserted into the bristle insertion holes.

Embodiment 22: The light irradiating toothbrush of embodiment 21 further comprising a waterproof plate coupled to a lower side of the bristle support plate.

Embodiment 23: The light irradiating toothbrush of embodiment 22 further comprising an optical means disposed on the waterproof plate for condensing or dispersing the light traveling from the lower side of the waterproof plate toward the bristles.

Embodiment 24: The light irradiating toothbrush of embodiment 23, wherein the optical means is disposed on an upper side of the waterproof plate.

Embodiment 25: The light irradiating toothbrush of embodiment 23, wherein the optical means is disposed on a lower side of the waterproof plate.

Embodiment 26: The light irradiating toothbrush of embodiment 23, wherein the optical means comprises a concave lens, a convex lens, a plana-concave lens, a double-concave lens, a plano-convex lens, a double-convex lens, or a combination thereof.

Embodiment 27: The light irradiating toothbrush of embodiment 23, wherein the optical means comprises a positive-meniscus lens or a negative-meniscus lens.

Embodiment 28: The light irradiating toothbrush of embodiment 27, wherein the bristle support plate and the waterproof plate match a shape of the optical means.

Embodiment 29: The light irradiating toothbrush of embodiment 1, wherein the bristle plate is detachable from the head.

Embodiment 30: The light irradiating toothbrush of embodiment 29 further comprising a detaching switch such that when the detaching switch is actuated, the bristle support plate detaches from the head.

Embodiment 31: The light irradiating toothbrush of embodiment 23, wherein the optical means is aligned to the plurality of bristle insertion holes.

Embodiment 32: The light irradiating toothbrush of embodiment 23, wherein the optical means is aligned between the plurality of bristle insertion holes.

Embodiment 33: The light irradiating toothbrush of embodiment 22 further comprising a light path controller disposed on an upper side of the waterproof plate capable of condensing or dispersing light from the light source unit.

Embodiment 34: The light irradiating toothbrush of embodiment 33, wherein at least a portion of the light path controller comprises a lens selected from a group consisting of a plano-concave lens, a double-concave lens, a plano-convex lens, a double-convex lens, a positive meniscus lens, and a negative meniscus lens.

Embodiment 35: The light irradiating toothbrush of embodiment 34, wherein each bristle insertion hole of the bristle support plate comprises an optical axis portion matching a shape of the lens.

Embodiment 36: The light irradiating toothbrush of embodiment 1 further comprising an ultrasonic wave generating device disposed in the head or the grip for generating ultrasonic waves to dean the bristles.

Embodiment 37: The light irradiating toothbrush of embodiment 1 further comprising: one or more health information sensors capable of sensing a heartbeat, pulse, and blood pressure of a user; a processor disposed in the grip, communicatively coupled to the one or more health information sensors, capable of receiving the heartbeat, pulse, and blood pressure and generating health information of the user; and a health information display communicatively coupled to the processor, disposed on a surface of the grip, capable of displaying the health information of the user.

Embodiment 38: The light irradiating toothbrush of embodiment 37, wherein the one or more health information sensors are disposed in the grip.

Embodiment 39: The light irradiating toothbrush of embodiment 37, wherein the one or more health information sensors are disposed in the head under the light source unit.

Embodiment 40: The light irradiating toothbrush of embodiment 37, wherein the one or more health information sensors comprise a reflectance oximetry sensor.

Embodiment 41: The light irradiating toothbrush of embodiment 37, wherein the processor is further capable of transmitting the health information to a health information department database.

Embodiment 42: The light irradiating toothbrush of embodiment 37 further comprising a power supply disposed in the grip, operatively coupled to the light source unit, the health information display, the processor, and the one or more health information sensors.

Embodiment 43: A light irradiating toothbrush comprising: a grip; a head operatively coupled to the grip, wherein the head includes a detachable bristle plate in which brushing bristles made of at least one waveguide are disposed; and a light source unit disposed under the bristle plate inside the head that includes a plurality of light sources radiating light through the waveguides of the brushing bristles, wherein the light source unit includes a light source comprising a plurality of lights each capable of radiating a plurality of wavelengths of light; further wherein the plurality of lights is a set of lights including a first sub-set that includes at least one first light source radiating a first light, and a second sub-set that includes at least one second light source radiating a second light, and the light sources of the light source unit are alternately arranged under the bristle plate.

The reference numbers recited in the below claims are solely for ease of examination of this patent application, and are exemplary, and are not intended in any way to limit the scope of the claims to the particular features having the corresponding reference numbers in the drawings.

What is claimed is:
1. A light irradiating toothbrush comprising:
a grip;
a head operatively coupled to the grip, wherein the head includes a detachable bristle plate in which brushing bristles made of at least one waveguide are disposed; and
a light source unit disposed inside the head and under the bristle plate that includes a plurality of light sources radiating light through the waveguides of the brushing bristles, wherein the light source unit includes a first light source radiating short-wavelength light and a second light source radiating long-wavelength light, the short-wavelength light source and the long-wavelength light source being disposed at different distances from the bristle plate, in accordance with the magnitude of the wavelengths, further wherein the plurality of light sources is a set of light sources including a first sub-set that includes at least one first light source radiating short-wavelength light, and a second sub-set that includes at least one second light source radiating long-wavelength light, and the light sources of the light source unit are alternately arranged under the bristle plate, wherein the light irradiating toothbrush further comprising a back light source unit under the bristle plate inside the head that includes a plurality of back light sources radiating light to a back of the head, wherein the back light source unit includes a first back light source radiating short-wavelength light and a second back light source radiating long-wavelength light, the short-wavelength light source and the long-wavelength light source being disposed at different distances from the back of the head, in accordance with the magnitude of the wavelengths, further wherein the plurality of back light sources is a set of light sources including a first sub-set that includes at least one first back light source radiating short-wavelength light, and a second sub-set that includes at least one second back light source radiating long-wavelength light, and the light sources of the back light source unit are alternately arranged under the bristle plate.

2. The light irradiating toothbrush of claim 1, wherein the short-wavelength light is blue light and the long-wavelength light is red light.

3. The light irradiating toothbrush of claim 1, wherein the light sources are arranged in a longitudinal direction of the head.

4. The light irradiating toothbrush of claim 1, wherein the light sources are LEDs (Light-Emitting Diode) or laser diodes.

5. The light irradiating toothbrush of claim 1, wherein the light source unit includes a first light source radiating short-wavelength light and second light source radiating long-wavelength light, and
the first light source is positioned closer to the brushing bristles than the second light source.

6. The light irradiating toothbrush of claim 1, wherein the brushing bristles are optical fibers.

7. The light irradiating toothbrush of claim 1, further comprising a vibrating motor and a substrate on which the light sources are disposed,
wherein the substrate comprises a first substrate and a second substrate, the first substrate being disposed in the grip, the second substrate being disposed in the head, the light source unit being disposed on the second substrate, wherein the vibrating motor is connected to the second substrate and vibrates the second substrate.

8. The light irradiating toothbrush of claim 1, wherein the bristle plate in the head further includes massaging bristles formed by a bundle of a plurality of waveguides or a plurality of optical fibers.

9. The light irradiating toothbrush of claim 8, wherein the massaging bristles further include capsules covering the massaging bristles.

10. The light irradiating toothbrush of claim 1 further comprising one or more walls disposed alongside the light source unit or between the plurality of light sources, wherein the one or more walls guide the short-wavelength light and the long-wavelength light towards a mouth of a user.

11. The light irradiating toothbrush of claim 1, wherein the light source unit comprises a plurality of forms selected from a group consisting of concave dents, convex dents, embossments, or a combination thereof, wherein each light source of the plurality of light sources directs light through a form of the plurality of forms.

12. A light irradiating toothbrush comprising:
a grip;
a head operatively coupled to the grip, wherein the head includes a detachable bristle plate in which brushing bristles made of at least one waveguide are disposed; and
a light source unit disposed inside the head and under the bristle plate that includes a plurality of light sources radiating light through the waveguides of the brushing bristles, wherein the light source unit includes a first light source radiating short-wavelength light and a second light source radiating long-wavelength light, the short-wavelength light source and the long-wavelength light source being disposed at different distances from the bristle plate, in accordance with the magnitude of the wavelengths, further wherein the plurality of light sources is a set of light sources including a first sub-set that includes at least one first light source radiating short-wavelength light, and a second sub-set that includes at least one second light source radiating long-wavelength light, and the light sources of the light source unit are alternately arranged under the bristle plate, wherein the light irradiating toothbrush further comprising a bristle support plate having a plurality of bristle insertion holes in which the plurality of bristles are inserted such that the bristle support plate supports the bristles at least partially inserted into the bristle insertion holes;

a waterproof plate coupled to a lower side of the bristle support plate; and an optical means disposed on the waterproof plate for condensing or dispersing the light traveling from the lower side of the waterproof plate toward the bristles.

13. The light irradiating toothbrush of claim 12, wherein the optical means comprises a concave lens, a convex lens, a plano-concave lens, a double-concave lens, a plano-convex lens, a double-convex lens, a positive-meniscus lens, a negative-meniscus lens, or a combination thereof.

14. The light irradiating toothbrush of claim 1 further comprising an ultrasonic wave generating device disposed in the head or the grip for generating ultrasonic waves to clean the bristles.

15. The light irradiating toothbrush of claim 1 further comprising:
a. one or more health information sensors capable of sensing a heartbeat, pulse, and blood pressure of a user;
b. a processor disposed in the grip, communicatively coupled to the one or more health information sensors, capable of receiving the heartbeat, pulse, and blood pressure and generating health information of the user; and
c. a health information display communicatively coupled to the processor, disposed on a surface of the grip, capable of displaying the health information of the user.

16. The light irradiating toothbrush of claim 15, wherein the one or more health information sensors are disposed in the grip, in the head under the light source unit, or a combination thereof.

* * * * *